US009956266B2

(12) United States Patent
Caggiano et al.

(10) Patent No.: US 9,956,266 B2
(45) Date of Patent: *May 1, 2018

(54) THERAPEUTIC DOSING OF A NEUREGULIN OR A SUBSEQUENCE THEREOF FOR TREATMENT OR PROPHYLAXIS OF HEART FAILURE

(71) Applicant: Acorda Therapeutics, Inc., Ardsley, NY (US)

(72) Inventors: Anthony O. Caggiano, Larchmont, NY (US); Anindita Ganguly, White Plains, NY (US); Jennifer Iaci, Boonton, NJ (US); Tom Parry, Hellertown, PA (US)

(73) Assignee: Acorda Therapeutics, Inc., Ardsley, NY (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/928,124

(22) Filed: Oct. 30, 2015

(65) Prior Publication Data

US 2016/0113999 A1    Apr. 28, 2016

Related U.S. Application Data

(63) Continuation of application No. 13/904,654, filed on May 29, 2013, now Pat. No. 9,198,951, which is a continuation of application No. 13/055,397, filed as application No. PCT/US2009/004130 on Jul. 17, 2009, now abandoned.

(60) Provisional application No. 61/135,171, filed on Jul. 17, 2008.

(51) Int. Cl.
*A61K 38/18* (2006.01)
*C07K 14/475* (2006.01)

(52) U.S. Cl.
CPC .......... *A61K 38/1883* (2013.01); *A61K 38/18* (2013.01)

(58) Field of Classification Search
None
See application file for complete search history.

(56) References Cited

U.S. PATENT DOCUMENTS

| | | |
|---|---|---|
| 5,530,109 A | 6/1996 | Goodearl et al. |
| 5,716,930 A | 2/1998 | Goodearl et al. |
| 6,051,401 A | 4/2000 | Chan et al. |
| 6,635,249 B1 | 10/2003 | Marchionni et al. |
| 7,037,888 B1 | 5/2006 | Sklar et al. |
| 7,226,907 B1 | 6/2007 | Zhou |
| 7,384,756 B1 | 6/2008 | Sklar et al. |
| 7,776,817 B2 | 8/2010 | Ford |
| 7,964,555 B2 | 6/2011 | Zhou |
| 7,973,007 B2 | 7/2011 | Ford |
| 9,198,951 B2 | 12/2015 | Caggiano et al. |
| 2006/0194734 A1 | 8/2006 | Zhou |
| 2007/0129296 A1 | 6/2007 | Zhou |
| 2007/0213264 A1 | 9/2007 | Zhou |

FOREIGN PATENT DOCUMENTS

| | | |
|---|---|---|
| CN | 1138785 C | 2/2004 |
| JP | 2002542270 A | 12/2002 |
| JP | 2003527337 A | 9/2003 |
| JP | 2004339238 A | 12/2004 |
| JP | 2005525317 A | 8/2005 |
| JP | 2005532332 A | 10/2005 |
| JP | 2006265244 A | 10/2006 |
| JP | 2009522209 A | 6/2009 |
| JP | 5797112 B2 | 10/2015 |
| RU | 2457854 C2 | 8/2012 |
| WO | WO-9615812 A1 | 5/1996 |
| WO | WO-9709425 A1 | 3/1997 |
| WO | WO-0018419 A2 | 4/2000 |
| WO | WO-0037095 A1 | 6/2000 |
| WO | WO-0064400 A2 | 11/2000 |
| WO | WO-0134174 A2 | 5/2001 |
| WO | WO-0189568 A1 | 11/2001 |
| WO | WO-03061571 A2 | 7/2003 |
| WO | WO-03099300 A1 | 12/2003 |
| WO | WO-06101691 A1 | 9/2006 |
| WO | WO-07076701 A1 | 7/2007 |
| WO | WO-09108390 A2 | 9/2009 |
| WO | WO-10030317 A2 | 3/2010 |
| WO | WO-11047183 A2 | 4/2011 |
| WO | WO-12021818 A2 | 2/2012 |
| WO | WO-13149163 A1 | 10/2013 |

OTHER PUBLICATIONS

"Consensus Recommendations for the Management of Chronic Heart Failure." *Am. J. Cardiol.* 83.2A(1999):1A-38A.
Acorda Therapeutics, Inc. *Acorda Therapeutics Reports First Quarter 2014 Financial Results.* N.p., May 6, 2014. Web. May 27, 2014. http://ir.acorda.com/investors/investor-news/investor-news-details/2014/Acorda-Therapeutics-Reports-First-Quarter-2014-Financial-Results/default.aspx.
Acorda Therapeutics, Inc. *Acorda Therapeutics Reports Fourth Quarter and Full Year 2013 Financial Results.* N. p., Feb. 13, 2014. Web. May 23, 2014.
Acorda Therapeutics, Inc. *Form 10-Q (Quarterly Report)*, Filed May 9, 2014 for the Period Ending Mar. 31, 14. Web. May 27, 2014. http://acorda.q4cdn.com/bbc4e76c-a4b3-4756-be21-30a3e90b9d2f.pdf?noexit-true.
Arbustini et al. "Coexistence of Mitochondrial DNA and β Myosin Heavy Chain Mutations in Hypertrophic Cardiomyopathy With Late Congestive heart Failure." *Heart.* 80.6(1998):548-558.
Bachinski et al. "New Theories: Causes of Dilated Cardiomyopathy." *Cardiol. Clin.* 16.4(1998):603-610.

(Continued)

Primary Examiner — Christine J Saoud
Assistant Examiner — Jon M Lockard
(74) *Attorney, Agent, or Firm* — Mintz Levin Cohn Ferris Glovsky and Popeo, P.C.

(57) ABSTRACT

The invention relates to treatment of heart failure in a mammal. Accordingly, the invention is directed to establishing a dosing regimen whereby the therapeutic benefits conferred by administration of a neuregulin such as glial growth factor 2 (GGF2) or a subsequence thereof are maintained and/or enhanced, while concomitantly minimizing any potential side effects.

12 Claims, 20 Drawing Sheets

(56) References Cited

OTHER PUBLICATIONS

Bian et al. "Neuregulin-1 Attenuated Doxorubicin-Induced Decrease in Cardiac Troponins." *Am. J. Physiol. Heart Circ. Physiol.* 297.6(2009):H1974-H1983.
Bublil et al. "The EGF Receptor Family: Spearheading a Merger of Signaling and Therapeutics." *Curr. Opin. Cell Biol.* 19.2(2007):124-134.
Buonanno et al. "Neuregulin and ErbB Receptor Signaling Pathways in the Nervous System." *Curr. Opin. Neurobiol.* 11.3(2001):287-296.
Burden et al. "Neuregulins and Their Receptors: A Versatile Signaling Module in Organogenesis and Oncogenesis." *Neuron.* 18.6(1997):847-855.
Busfield et al. "Characterization of a Neuregulin-Related Gene, Don-1, That is Highly Expressed in Restricted Regions of the Cerebellum and Hippocampus." *Mol. Cell. Biol.* 17.7(1997):4007-4014.
Carraway et al. "Neuregulin-2, a New Ligand of ErbB3/ErbB4-Receptor Tyrosine Kinases." *Nature.* 387(1997):512-516.
Chang et al. "Ligands for ErbB-Family Receptors Encoded by a Neuregulin-Like Gene." *Nature.* 387(1997):509-512.
Chen et al. "Expression of Multiple Neuregulin Transcripts in Postnatal Rat Brains." *J. Comp. Neurol.* 349.3(1994):389-400.
Cohn et al. "A Dose-Dependent Increase in Mortality With Vesnarinone Among Patients With Severe Heart Failure." *N. Engl. J. Med.* 339(1998):1810-1816.
Corfas et al. "Differential Expression of ARIA Isoforms in the Rat Brain." *Neuron.* 14.1(1995):103-115.
Falls. "Neuregulins: Functions, Forms, and Signaling Strategies." *Exp. Cell Res.* 284.1(2003):14-30.
Fukazawa et al. "Neuregulin-1 Protects Ventricular Myocytes From Anthracycline-Induced Apoptosis via erbB4-Dependent Activation of PI3-Kinase/Akt." *J. Mol. Cell Cardiol.* 35.12(2003):1473-1479.
Gassmann et al. "Aberrant Neural and Cardiac Development in Mice Lacking the ErbB4 Neuregulin Receptor." *Nature.* 378.6555(1995):390-394.
GenBank Accession No. AB005060, Nov. 11, 1997.
Higashiyama et al. "A Novel Brain-Derived Member of the Epidermal Growth Factor Family that Interacts with ErbB3 and ErbB4." *J. Biochem.* 122.3(1997):675-680.
Hijazi et al. "NRG-3 in Human Breast Cancers: Activation of Multiple erbB Family Proteins." *Int. J. Oncol.* 13.5(1998):1061-1067.
Holmes et al. "Identification of Heregulin, A Specific Activator of p185erbB2." *Science.* 256(1992):1205-1210.
Hynes et al. "ErbB Receptors and Signaling Pathways in Cancer." *Curr. Opin. Cell Biol.* 21.2(2009):177-184.
Iaci et al. "Glial Growth Factor 2 Promotes Functional Recovery With Treatment Initiated Up to 7 Days After Permanent Focal Ischemic Stroke." *Neuropharmacol.* 59.7-8(2010):640-649.
International Search Report issued in International Application No. PCT/US2013/034634 dated Jul. 2, 2013.
Kastin et al. "Neuregulin-1β1 Enters Brain and Spinal Cord by Receptor-Mediated Transport." *J. Neurochem.* 88.4(2004):965-970.
Lee et al. "Requirement for Neuregulin Receptor erbB2 in Neural and Cardiac Development." *Nature.* 378.6555(1995):394-398.
Lemke. "Neuregulins in Development." *Mol. Cell. Neurosci.* 7.4(1996):247-262.
Lijun et al. "A Progress in Research on Treatment of Chronic Cardiac Failure with Neuregulin." *J. Clin. Cardiol.* (China). 23.11(2007):803-805. (No English Translation Available).
Liu et al. "Neuregulin-1/erbB-Activation Improves Cardiac Function and Survival in Models of Ischemic, Dilated, and Viral Cardiomyopathy." *J. Am. Coll. Cardiol.* 48.7(2006):1438-1447.
Marchionni et al. "Glial Growth Factors are Alternatively Spliced erbB2 Ligands Expressed in the Nervous System." *Nature.* 362(1993):312-318.
Meyer et al. "Distinct Isoforms of Neuregulin are Expressed in Mesenchymal and Neuronal Cells During Mouse Development." *PNAS.* 91.3(1994):1064-1068.
Meyer et al. "Isoform-Specific Expression and Function of Neuregulin." *Development.* 124(1997):3575-3586.
Meyer et al. "Multiple Essential Functions of Neuregulin in Development." *Nature.* 378(1995):386-390.
Nagata et al. "Solution Structure of the Epidermal Growth Factor-Like Domain of Heregulin-α, a Ligand for p180erbB-4." *EMBO J.* 13.15(1994):3517-3523.
Orr-Urtreger et al. "Neural Expression and Chromosomal Mapping of Neu Differentiation Factor to 8p12-p21." *PNAS.* 90.5(1993):1867-1871.
Peles et al. "Isolation of the Neu/HER-2 Stimulatory Ligand: A 44 kd Glycoprotein That Induces Differentiation of Mammary Tumor Cells." *Cell.* 69.1(1992):205-216.
Peles et al. "Neu and its Ligands: From an Oncogene to Neural Factors." *BioEssays.* 15.12(1993):815-824.
Pinkas-Kramarski et al. "Brain Neurons and Glial Cells Express Neu Differentiation Factor/Heregulin: A Survival Factor for Astrocytes." *PNAS.* 91.20(1994):9387-9391.
Pinkas-Kramarski et al. "Differential Expression of NDF/Neuregulin Receptors ErbB-3 and ErbB-4 and Involvement in Inhibition of Neuronal Differentiation." *Oncogene.* 15(1997):2803-2815.
Pinkas-Kramarski et al. "ErB Tyrosine Kinases and the Two Neuregulin Families Constitute a Ligand-Receptor Network." *Mol. Cell. Biol.* 18.10(1998):6090-6101.
Sawyer et al. "Neuregulin-1β for the Treatment of Systolic Heart Failure." *J. Mol. Cell Cardiol.* 51.4(2011):501-505.
Siu et al. "Familial Dilated Cardiomyopathy Locus Maps to Chromosome 2q31." *Circulation.* 99(1999):1022-1026.
SOLVD Investigators. "Effect of Enalapril on Mortality and the Development of Heart Failure in Asymptomatic Patients With Reduced Left Ventricular Ejection Fractions." *N. Engl. J. Med.* 327.10(1992):685-691.
Stewart et al. "More 'Malignant' Than Cancer? Five-Year Survival Following a First Admission for Heart Failure." *Eur. J. Heart Fail.* 3.3(2001):315-322.
Sutherland et al. "Neuroprotection for Ischaemic Stroke: Translation From the Bench to the Bedside." *Int. J. Stroke.* 7.5(2012):407-418.
Wen et al. "Neu Differentiation Factor: A Transmembrane Glycoprotein Containing an EGF Domain and an Immunoglobulin Homology Unit." *Cell.* 69.3(1992):559-572.
Williams et al. "Agrin and Neureglin, Expanding Roles and Implications for Therapeutics." *Biotechnol. Adv.* 26.3(2008):187-201.
Xu et al. "Extended Therapeutic Window and Functional Recovery After Intraarterial Administration of Neuregulin-1 After Focal Ischemic Stroke." *J. Cerebral Blood Flow Metab.* 26(2005):527-535.
Zhang et al. "Neuregulin-3 (NRG3): A Novel Neural Tissue-Enriched Protein That Binds and Activates ErbB4." *PNAS.* 94.18(1997):9562-9567.
Özcelik et al. "Conditional Mutation of the ErbB2 (HER2) Receptor in Cardiomyocytes Leads to Dilated Cardiomyopathy." *PNAS.* 99.13(2002):8880-8885.
Harari et al., Neuregulin-4: a novel growth factor that acts through the ErbB-4 receptor tyrosine kinase. Oncogene. Apr. 29, 1999;18(17):2681-9.

Nucleotide Sequence & Deduced Acid Sequence of GGF2HBS5

```
GGAATTCCTT TTTTTTTTT TTTTTTTTCTT NNTTTTTTT TGCCCTTATA CCTCCTCGCC         60
TTTCTGGT TCCATCCACT TCTTCCCCCT CCTCCTCCCA TAAACAACTC TCCTACCCCT        120
GCACCCCCAA TAAATAAATA AAAGGAGGAG GGCAAGGGGG GAGGAGGAGG AGTGGTGCTG        180
CGAGGGGAAG GAAAGGGAG GCAAGCGTCAG AAGAGCCCGA CAGAGTCCGA ACCGACAGCC        240
AGAAGTCCGC ACCGACCTCG CAC ATG AGA TGG CGA CGT GCC CCG CGC CGC           291
                            Met Arg Trp Arg Arg Ala Pro Arg Arg
TCC GGT CCC CCC CGG GCC CCC CAG CGC CCC GGC TCC GCC GCC CGC             339
Ser Gly Pro Pro Arg Ala Pro Gln Arg Pro Gly Ser Ala Ala Arg
TCG CCG CCG CTG CCG CCA CTA CGG CTG CTG CTG CTG GGG ACC                 387
Ser Pro Pro Leu Pro Leu Pro Leu Leu Leu Leu Leu Gly Thr
                                          Val Cys Leu Thr Val
                                                       GGF-II 09
GCG GCC CTG GCA CCG GGG GCG GCC GGC AAC GAG GCG GCT CCC GCG             435
Ala Ala Leu Ala Pro Gly Ala Ala Gly Asn Glu Ala Ala Pro Ala
Ala Leu Pro Pro
GGG GCC TCG GTG TGC TAC TCG TCC CCG CCC AGC GTG GGA TCG GTG CAG         483
Gly Ala Ser Val Cys Tyr Ser Ser Pro Pro Ser Val Gly Ser Val Gln
                   Ala Ser Pro Val Ile Val Ser Val Gly Ser Val Gln
                                                       GGF-II 08
GAG CTA GCT TAC CGC GCC GCG GTG GTG ATC GAG GGA AAG GTG CAC CCG         531
Glu Leu Ala Gln Arg Ala Ala Val Val Ile Glu Gly Lys Val His Pro
Glu Leu Val Gln Arg Trp Phe Val Val Ile Glu Gly Lys
                                       GGF-II 04
```

FIG. 8A

Nucleotide Sequence & Deduced Acid Sequence of GGF2HBS5

```
CAG CGG CAG GGG GCA CTC GAC AGG AAG GCG GCG GCG GCG          579
Gln Arg Gln Gly Ala Leu Asp Arg Lys Ala Ala Ala Ala

GGC GCA GGG GCG TGG GGC GAT GGC GAG CCA GCC GCC GGC          627
Gly Ala Gly Ala Trp Gly Asp Gly Glu Pro Ala Ala Gly

CCA CGG GCC CTG GGG CCC GCC GAG CTG CTC GCC GCC AAC          675
Pro Arg Ala Leu Gly Pro Ala Glu Leu Leu Ala Ala Asn
           GGF-II 03

GGG ACC GTG CCC TGT CCC ACC GTG CCC AGC GGG GAG              723
Gly Thr Val Pro Cys Pro Thr Val Pro Ser Ala Gly Glu

CCC GGG GAG GCG CCC TAT CTG GTG AAG GTG GTG CAG GTG TGG GCG  771
Pro Gly Glu Ala Pro Tyr Leu Val Lys Val His Gln Val Trp Ala
                                Lys Val His Glu Val Trp Ala
                                      GGF-II 01 & GGF-II 11

GTG AAA GCC GGG GGC TTG GGG AAG GAC TCG CTC CTC ACC GTG CGC CTG    819
Val Lys Ala Gly Gly Leu Gly Lys Asp Ser Leu Leu Thr Val Arg Leu
Ala Lys                           Asp Leu Leu Xaa Val     Leu
                                           GGF-II 10

GGG ACC TGC GGC CAC CCC GCC TTC CCC GCC TCC GGG AGG CTC AAG CAG    867
Gly Thr Trp Gly His Pro Ala Phe Pro Ala Ser Gly Arg Leu Lys Glu
Gly Ala Trp Gly Pro Pro Ala Phe Pro Val Xaa Tyr
      GGF-II 02

GAC AGC AGG TAC ATC TTC ATG GAG CCC GAC GCC AAC AGC ACC AGC        915
Asp Ser Arg Tyr Ile Phe Met Glu Pro Asp Ala Asn Ser Thr Ser
Tyr Ile Phe Met Glu Pro Gly Ala Xaa Ser Gly
```

FIG. 8B

Nucleotide Sequence & Deduced Acid Sequence of GGF2HBS5

```
CGC GCG CCG GCC TTC CGA GCC TCT TTC CCC CCT CTG GAG ACG GGC      963
Arg Ala Pro Ala Phe Arg Ala Ser Phe Pro Pro Leu Glu Thr Gly

CGG AAC CTC AAG GAG AAG GTC AGC CGG TGC CTG AAG CGG TGC GCC     1011
Arg Asn Leu Lys Glu Lys Val Ser Arg Cys Leu Lys Arg Cys Ala

TTG CCT CCC CAA TTG AAA GAG ATG AAA AGC CAG GCT TCG GCA GGT     1059
Leu Pro Pro Gln Leu Lys Glu Met Lys Ser Gln Ser Ala Ala Gly
                                                    GGF-II 12
TCC AAA CTA GTC CTT CGG TGT GAA ACC TCT TCT GAA TAC TCC TCT CTC 1107
Ser Lys Val Leu Arg Cys Glu Thr Ser Ser Glu Tyr Ser Ser Leu
    Leu Val Leu Arg
    GGF-II 06

AGA TTC AAG TGG TTC AAG AAT GGG AAT GAA TTC AAT CGA AAA AAC AAA 1155
Arg Phe Lys Trp Phe Lys Asn Gly Asn Glu Phe Asn Arg Lys Asn Lys

CCA CAA AAT ATC AAG ATA CAA AAA AAG CCA GGG AAG TCA GAA CTT CGC 1203
Pro Gln Asn Ile Lys Ile Gln Lys Lys Pro Gly Lys Ser Glu Leu Arg

ATT AAC AAA GCA TCA CTG GCT GAT TCT GGA GAG TAT ATG TGC AAA GTG 1251
Ile Asn Lys Ala Ser Leu Ala Asp Ser Gly Glu Tyr Met Cys Lys Val
    Lys Ala Ser Leu Ala Asp Ser Gly Glu Tyr Met Xaa Lys

ATC AGC AAA TTA GGA AAT GAC AGT GCC TCT GCC AAT ATC ACC ATC GTG 1299
Ile Ser Lys Leu Gly Asn Asp Ser Ala Ser Ala Asn Ile Thr Ile Val

GAA TCA AAC GCT ACA TCT ACA ACC TCC ACA ACT GGG ACA AGC CAT CTT GTA 1347
Glu Ser Asn Ala Thr Ser Thr Thr Ser Thr Thr Gly Thr Ser His Leu Val
```

FIG. 8C

Nucleotide Sequence & Deduced Acid Sequence of GGF2HBS5

```
AAA TGT GCG GAG AAG GAG AAA ACT TAC TGT GTG AAT GGA GGG GAG TGC     1395
Lys Cys Ala Glu Lys Glu Lys Thr Tyr Cys Val Asn Gly Gly Glu Cys

TTC ATG GTG AAA GAC CTT TCA AAC CCC TCA AGA TAC TTG TGC AAG TGC     1443
Phe Met Val Lys Asp Leu Ser Asn Pro Ser Arg Tyr Leu Cys Lys Cys

CCA AAT CAG TTT ACT GGT GAT CGC TGC CAA AAC TAC GTA ATG GCC AGC     1491
Pro Asn Gln Phe Thr Gly Asp Arg Cys Gln Asn Tyr Val Met Ala Ser

TTC TAC AGT ACG TCC ACT CCC TTT CTG TCT CCT GAA                     1530
Phe Tyr Ser Thr Ser Thr Pro Phe Leu Ser Pro Glu

TAGGAGCATG CTCAGTTGGT GCTGCTTTCT TGTTGCTGCA TCTCCCTCA GATTCCACCT    1590
AGAGCTAGAT GTGTCTTACC AGATCTAATA TTGACTGCCT CTGCCTGTCG CATGAGAACA   1650
TTAACAAAAG CAATTGTATT ACTTCCCTCG TTCGCGACTA GTTGGCTCTG AGATACTAAT   1710
AGGTGTGTGA GGCTCCGGAT GTTTCTGGAA TTGATATTGA ATGATGTGAT ACAAATTGAT   1770
AGTCAATATC AAGCAGTCAA ATATGATAAT AAAGGCATTT CAAAGTCTCA CTTTTATTGA   1830
TAAAATAAAA ATCATTCTAC TGAACAGTCC ATCTCTTTA TACAATGACC ACATCCTGAA    1890
AAGGGTGTTG CTAAGCTGTA ACCGATATGC ACTTGAAATG ATGGTAAGTT AATTTGATT    1950
CAGAATGTGT TATTTGTCAC AAATAAACAT AATAAAGGA AAAAAAAAAA AAA           2003
```

FIG. 8D

EGFL1

| | | | | | | | | | | | | | | | |
|---|---|---|---|---|---|---|---|---|---|---|---|---|---|---|---|
| AGC | CAT | CTT | GTC | AAG | TGT | GCA | GAG | AAG | GAG | AAA | ACT | TTC | TGT | GTG | AAT | 48 |
| Ser | His | Leu | Val | Lys | Cys | Ala | Glu | Lys | Glu | Lys | Thr | Phe | Cys | Val | Asn |
| GGA | GGC | GAG | TGC | TTC | ATG | GTG | TTT | AAA | GAC | CTT | TCA | AAT | CCC | TCA | AGA | TAC | 96 |
| Gly | Gly | Glu | Cys | Phe | Met | Val | Phe | Lys | Asp | Leu | Ser | Asn | Pro | Ser | Arg | Tyr |
| TTG | TGC | AAG | TGC | CCA | AAT | GAG | TTT | ACT | GGT | GAT | CGC | TGC | CAA | AAC | TAC | 144 |
| Leu | Cys | Lys | Cys | Pro | Asn | Glu | Phe | Thr | Gly | Asp | Arg | Cys | Gln | Asn | Tyr |
| GTA | ATG | GCC | AGC | TTC | TAC | AGT | ACG | TCC | ACT | CCC | TTT | CTG | TCT | CTG | CCT | 192 |
| Val | Met | Ala | Ser | Phe | Tyr | Ser | Thr | Ser | Thr | Pro | Phe | Leu | Ser | Leu | Pro |
| GAA | TAG | | | | | | | | | | | | | | | 198 |
| Glu |

FIG. 9

EGFL2

```
AGC CAT CTT GTC AAG TGT GCA GAG AAA ACT TTC TGT GTG AAT    48
Ser His Leu Val Lys Cys Ala Glu Lys Thr Phe Cys Val Asn

GGA GGC GAG TGC TTC ATG GTG AAA GAC CTT TCA AAT CCC TCA AGA TAC    96
Gly Gly Glu Cys Phe Met Val Lys Asp Leu Ser Asn Pro Ser Arg Tyr

TTC TGC AAG TGC CAA CCT GGA TTC ACT GGA GCG AGA TGT ACT GAG AAT    144
Leu Cys Lys Cys Gln Pro Gly Phe Thr Gly Ala Arg Cys Thr Glu Asn

GTG CCC ATG AAA GTC CAA ACC CAA GAA AAA GCG GAG GAG CTC TAC TAA    192
Val Pro Met Lys Val Gln Thr Gln Glu Lys Ala Glu Glu Leu Tyr
```

FIG. 10

EGFL3

| | | | | | | | | | | | | | | | |
|---|---|---|---|---|---|---|---|---|---|---|---|---|---|---|---|
|AGC|CAT|CTT|GTC|AAG|TGT|GCA|GAG|AAG|GAG|AAA|ACT|TTC|TGT|GTG|AAT| 48
|Ser|His|Leu|Val|Lys|Cys|Ala|Glu|Lys|Glu|Lys|Thr|Phe|Cys|Val|Asn|

| | | | | | | | | | | | | | | | |
|---|---|---|---|---|---|---|---|---|---|---|---|---|---|---|---|
|GGA|GGC|GAG|TGC|TTC|ATG|GTG|AAA|GAC|CTT|TCA|AAT|CCC|TCA|AGA|TAC| 96
|Gly|Gly|Glu|Cys|Phe|Met|Val|Lys|Asp|Leu|Ser|Asn|Pro|Ser|Arg|Tyr|

| | | | | | | | | | | | | | | | |
|---|---|---|---|---|---|---|---|---|---|---|---|---|---|---|---|
|TTC|TGC|AAG|TGC|CCA|AAT|GAG|TTT|ACT|GGT|GAT|CGC|TGC|CAA|AAC|TAC| 144
|Leu|Cys|Lys|Cys|Pro|Asn|Glu|Phe|Thr|Gly|Asp|Arg|Cys|Gln|Asn|Tyr|

| | | | | | | | | | | | | |
|---|---|---|---|---|---|---|---|---|---|---|---|---|
|GTA|ATG|GCC|AGC|TTC|TAC|AAA|GCG|GAG|CTC|TAC|TAA| | 183
|Val|Met|Ala|Ser|Phe|Tyr|Lys|Ala|Glu|Leu|Tyr| | |

FIG. 11

EGFL4

```
AGC CAT CTT GTC AAG TGT GCA GAG AAG GAG AAA ACT TTC TGT GTG AAT    48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC   144
Leu Cys Lys Cys Pro Asn Glu Phe Thr Gly Asp Arg Cys Gln Asn Tyr

GTA ATG GCC AGC TTC TAC AAG CAT CTT GGG ATT GAA TTT ATG GAG AAA   192
Val Met Ala Ser Phe Tyr Lys His Leu Gly Ile Glu Phe Met Glu Lys

GCG GAG CTC TAC TAA                                                210
Ala Glu Leu Tyr
```

FIG. 12

EGFL5

| | | | | | | | | | | | | | | | |
|---|---|---|---|---|---|---|---|---|---|---|---|---|---|---|---|
|AGC|CAT|CTT|GTC|AAG|TGT|GCA|GAG|AAG|GAG|AAA|ACT|TTC|TGT|GTG|AAT|48
|Ser|His|Leu|Val|Lys|Cys|Ala|Glu|Lys|Glu|Lys|Thr|Phe|Cys|Val|Asn|
|GGA|GGC|GAG|TGC|TTC|ATG|GTG|AAA|GAC|CTT|TCA|AAT|CCC|TCA|AGA|TAC|96
|Gly|Gly|Glu|Cys|Phe|Met|Val|Lys|Asp|Leu|Ser|Asn|Pro|Ser|Arg|Tyr|
|TTG|TGC|AAG|TGC|CAA|CCT|GGA|TTC|ACT|GGA|GCG|AGA|TGT|ACT|GAG|AAT|144
|Leu|Cys|Lys|Cys|Gln|Pro|Gly|Phe|Thr|Gly|Ala|Arg|Cys|Thr|Glu|Asn|
|GTG|CCC|ATG|AAA|GTC|CAA|ACC|CAA|GAA|AAG|TGC|CCA|AAT|GAG|TTT|ACT|192
|Val|Pro|Met|Lys|Val|Gln|Thr|Gln|Glu|Lys|Cys|Pro|Asn|Glu|Phe|Thr|
|GGT|GAT|CGC|TGC|CAA|AAC|TAC|GTA|ATG|GCC|AGC|TTC|TAC|AGT|ACG|TCC|240
|Gly|Asp|Arg|Cys|Gln|Asn|Tyr|Val|Met|Ala|Ser|Phe|Tyr|Ser|Thr|Ser|
|ACT|CCC|TTT|CTG|TCT|CTG|CCT|GAA|TAG| | | | | | | |267
|Thr|Pro|Phe|Leu|Ser|Leu|Pro|Glu| | | | | | | | |

FIG. 13

EGFL6

AGC CAT CTT GTC AAG TGT GCA GAG AAG GAG AAA ACT TTC TGT GTG AAT    48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
Gly Gly Glu Cys Phe Met Val Lys Asp Leu Ser Asn Pro Ser Arg Tyr

TTG TGC AAG TGC CAA CCT GGA TTC ACT GGA GCC AGA TGT ACT GAG AAT   144
Leu Cys Lys Cys Gln Pro Gly Phe Thr Gly Ala Arg Cys Thr Glu Asn

GTG CCC ATG AAA GTC CAA ACC CAA GAA AAG TGC CCA AAT GAG TTT ACT   192
Val Pro Met Lys Val Gln Thr Gln Glu Lys Cys Pro Asn Glu Phe Thr

GGT GAT CGC TGC CAA AAC TAC GTA ATG GCC AGC TTC TAC AAA GCG GAG   240
Gly Asp Arg Cys Gln Asn Tyr Val Met Ala Ser Phe Tyr Lys Ala Glu

GAG CTC TAC TAA                                                    252
Glu Leu Tyr

FIG. 14

Ser His Leu Val Lys Cys Ala Glu Lys Thr Phe Cys Val Asn

Gly Gly Glu Cys Phe Met Val Lys Asp Leu Ser Asn Pro Ser Arg Tyr

Leu Cys Lys Cys Pro Asn Glu Phe Thr Gly Asp Arg Cys Gln Asn Tyr

Val Met Ala Ser Phe Tyr Lys Ala Glu Glu Leu Tyr

FIG. 15

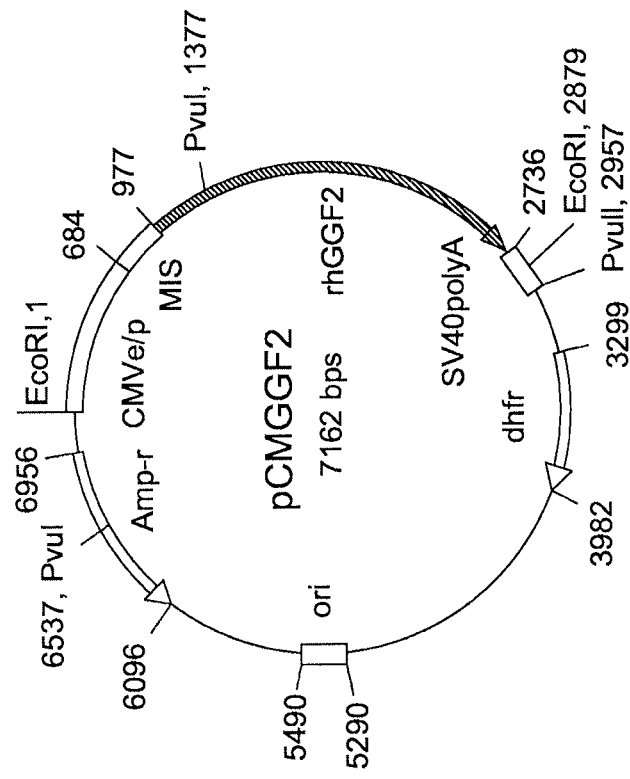
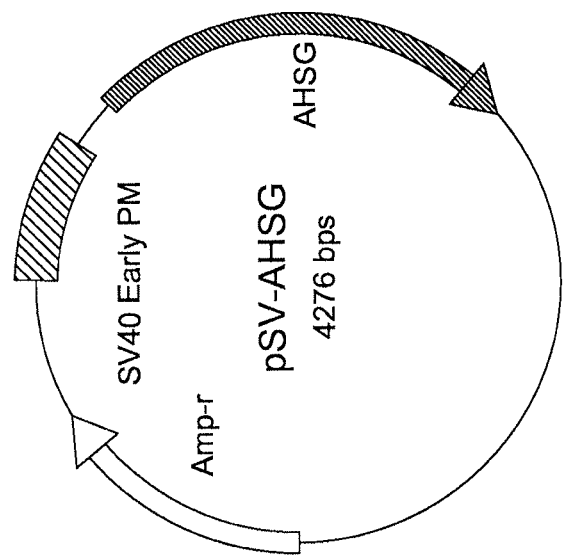
FIG. 16

SEQUENCE LISTING

```
<160> NUMBER OF SEQ ID NOS: 33

<210> SEQ ID NO 1
<211> LENGTH: 2003
<212> TYPE: DNA
<213> ORGANISM: Homo sapiens
<220> FEATURE:
<221> NAME/KEY: misc_feature
<222> LOCATION: (31)..(32)
<223> OTHER INFORMATION: n is a, c, g, or t

<400> SEQUENCE: 1
ggaattcctt tttttttttt ttttttttctt nnttttttttt tgcccttata cctcttcgcc      60
tttctgtggt tccatccact tcttcccct cctcctccca taaacaactc tcctaccct       120 gcaccccaa taaataaata aaaggaggag ggcaaggggg gaggaggagg agtggtgctg       180
cgaggggaag gaaaagggag gcagcgcgag aagagccggg cagagtccga accgacagcc      240
```

-continued

```
agaagcccgc acgcacctcg caccatgaga tggcgacgcg ccccgcgccg ctccgggcgt    300
cccggccccc gggcccagcg ccccggctcc gccgcccgct cgtcgccgcc gctgccgctg    360
ctgccactac tgctgctgct ggggaccgcg gccctggcgc cgggggcggc ggccggcaac    420
gaggcggctc ccgcgggggc ctcggtgtgc tactcgtccc cgcccagcgt gggatcggtg    480
caggagctag ctcagcgcgc cgcggtggtg atcgagggaa aggtgcaccc gcagcggcgg    540
cagcaggggg cactcgacag gaaggcggcg gcggcggcgg gcgaggcagg ggcgtggggc    600
ggcgatcgcg agccgccagc cgcgggccca cgggcgctgg ggccgcccgc cgaggagccg    660
ctgctcgccg ccaacgggac cgtgccctct tggcccaccg ccccggtgcc cagcgccggc    720
gagcccgggg aggaggcgcc ctatctggtg aaggtgcacc aggtgtgggc ggtgaaagcc    780
gggggcttga agaaggactc gctgctcacc gtgcgcctgc gcgcgccggc cgccttccga    840
gcctctttcc cccctctgga gacgggccgg aacctcaaga aggaggtcag ccgggtgctg    900
tgcaagcggt gcgccttgcc tccccaattg aaagagatga aaagccagga atcggctgca    960
ggttccaaac tagtccttcg gtgtgaaacc agttctgaat actcctctct cagattcaag   1020
tggttcaaga atgggaatga attgaatcga aaaaacaaac cacaaaatat caagatacaa   1080
aaaaagccag ggaagtcaga acttcgcatt aacaaagcat cactggctga ttctggagag   1140
tatatgtgca aagtgatcag caaattagga aatgacagtg cctctgccaa tatcaccatc   1200
gtggaatcaa acgctacatc tacatccacc actgggacaa gccatcttgt agggacctgg   1260
ggccaccccg ccttcccctc ctgcgggagg ctcaaggagg acagcaggta catcttcttc   1320
atggagcccg acgccaacag caccagcaaa tgtgcggaga aggagaaaac tttctgtgtg   1380
aatggagggg agtgcttcat ggtgaaagac ctttcaaacc cctcgagata cttgtgcaag   1440
tgcccaaatg agtttactgg tgatcgctgc caaaactacg taatggccag cttctacagt   1500
acgtccactc cctttctgtc tctgcctgaa taggagcatg ctcagttggt gctgctttct   1560
tgttgctgca tctcccctca gattccacct agagctagat gtgtcttacc agatctaata   1620
ttgactgcct ctgcctgtcg catgagaaca ttaacaaaag caattgtatt acttcctctg   1680
ttcgcgacta gttggctctg agatactaat aggtgtgtga ggctccggat gtttctggaa   1740
ttgatattga atgatgtgat acaaattgat agtcaatatc aagcagtgaa atatgataat   1800
aaaggcattt caaagtctca cttttattga taaaataaaa atcattctac tgaacagtcc   1860
atcttcttta tacaatgacc acatcctgaa aagggtgttg ctaagctgta accgatatgc   1920
acttgaaatg atggtaagtt aattttgatt cagaatgtgt tatttgtcac aaataaacat   1980
aataaaagga aaaaaaaaaa aaa                                           2003
```

<210> SEQ ID NO 2
<211> LENGTH: 406
<212> TYPE: PRT
<213> ORGANISM: Homo sapiens

<400> SEQUENCE: 2

```
Met Arg Trp Arg Arg Ala Pro Arg Arg Ser Gly Arg Pro Gly Pro Arg
1               5                   10                  15

Ala Gln Arg Pro Gly Ser Ala Ala Arg Ser Ser Pro Pro Leu Pro Leu
            20                  25                  30

Leu Pro Leu Leu Leu Leu Leu Gly Thr Ala Ala Leu Ala Pro Gly Ala
        35                  40                  45

Ala Ala Gly Asn Glu Ala Ala Pro Ala Gly Ala Ser Val Cys Tyr Ser
```

| | | | | | | |
|---|---|---|---|---|---|---|
| | 50 | | 55 | | 60 | |

Ser Pro Pro Ser Val Gly Ser Val Gln Glu Leu Ala Gln Arg Ala Ala
65                   70                  75                  80

Val Val Ile Glu Gly Lys Val His Pro Gln Arg Gln Gln Gly Ala
                85                  90                  95

Leu Asp Arg Lys Ala Ala Ala Ala Gly Glu Ala Gly Ala Trp Gly
            100                 105                 110

Gly Asp Arg Glu Pro Pro Ala Ala Gly Pro Arg Ala Leu Gly Pro Pro
            115                 120                 125

Ala Glu Glu Pro Leu Leu Ala Ala Asn Gly Thr Val Pro Ser Trp Pro
130                 135                 140

Thr Ala Pro Val Pro Ser Ala Gly Glu Pro Gly Glu Ala Pro Tyr
145                 150                 155                 160

Leu Val Lys Val His Gln Val Trp Ala Val Lys Ala Gly Gly Leu Lys
                165                 170                 175

Lys Asp Ser Leu Leu Thr Val Arg Leu Gly Thr Trp Gly His Pro Ala
            180                 185                 190

Phe Pro Ser Cys Gly Arg Leu Lys Glu Asp Ser Arg Tyr Ile Phe Phe
            195                 200                 205

Met Glu Pro Asp Ala Asn Ser Thr Ser Arg Ala Pro Ala Ala Phe Arg
210                 215                 220

Ala Ser Phe Pro Pro Leu Glu Thr Gly Arg Asn Leu Lys Lys Glu Val
225                 230                 235                 240

Ser Arg Val Leu Cys Lys Arg Cys Ala Leu Pro Pro Gln Leu Lys Glu
                245                 250                 255

Met Lys Ser Gln Glu Ser Ala Ala Gly Ser Lys Leu Val Leu Arg Cys
            260                 265                 270

Glu Thr Ser Ser Glu Tyr Ser Ser Leu Arg Phe Lys Trp Phe Lys Asn
            275                 280                 285

Gly Asn Glu Leu Asn Arg Lys Asn Lys Pro Gln Asn Ile Lys Ile Gln
290                 295                 300

Lys Lys Pro Gly Lys Ser Glu Leu Arg Ile Asn Lys Ala Ser Leu Ala
305                 310                 315                 320

Asp Ser Gly Glu Tyr Met Cys Lys Val Ile Ser Lys Leu Gly Asn Asp
            325                 330                 335

Ser Ala Ser Ala Asn Ile Thr Ile Val Lys Cys Ala Glu Lys Glu Lys
            340                 345                 350

Thr Phe Cys Val Asn Gly Gly Glu Cys Phe Met Val Lys Asp Leu Ser
            355                 360                 365

Asn Pro Ser Arg Tyr Leu Cys Lys Cys Pro Asn Glu Phe Thr Gly Asp
370                 375                 380

Arg Cys Gln Asn Tyr Val Met Ala Ser Phe Tyr Ser Thr Ser Thr Pro
385                 390                 395                 400

Phe Leu Ser Leu Pro Glu
            405

<210> SEQ ID NO 3
<211> LENGTH: 198
<212> TYPE: DNA
<213> ORGANISM: Homo sapiens
<400> SEQUENCE: 3
agccatcttg tcaagtgtgc agagaaggag aaaactttct gtgtgaatgg aggcgagtgc    60
ttcatggtga agacctttc aaatccctca agatacttgt gcaagtgccc aaatgagttt   120

```
actggtgatc gctgccaaaa ctacgtaatg gccagcttct acagtacgtc cactcccttt      180
ctgtctctgc ctgaatag                                                    198

<210> SEQ ID NO 4
<211> LENGTH: 65
<212> TYPE: PRT
<213> ORGANISM: Homo sapiens

<400> SEQUENCE: 4

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Ser Thr Ser Thr Pro Phe Leu Ser Leu Pro
    50                  55                  60

Glu
65

<210> SEQ ID NO 5
<211> LENGTH: 192
<212> TYPE: DNA
<213> ORGANISM: Homo sapiens

<400> SEQUENCE: 5
agccatcttg tcaagtgtgc agagaaggag aaaactttct gtgtgaatgg aggcgagtgc       60
ttcatggtga agacctttc aaatccctca agatacttgt gcaagtgcca acctggattc      120
actggagcga gatgtactga gaatgtgccc atgaaagtcc aaacccaaga aaaagcggag      180
gagctctact aa                                                          192

<210> SEQ ID NO 6
<211> LENGTH: 63
<212> TYPE: PRT
<213> ORGANISM: Homo sapiens

<400> SEQUENCE: 6

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Lys Val Gln Thr Gln Glu Lys Ala Glu Glu Leu Tyr
    50                  55                  60

<210> SEQ ID NO 7
<211> LENGTH: 183
<212> TYPE: DNA
<213> ORGANISM: Homo sapiens

<400> SEQUENCE: 7
agccatcttg tcaagtgtgc agagaaggag aaaactttct gtgtgaatgg aggcgagtgc       60
ttcatggtga agacctttc aaatccctca agatacttgt gcaagtgccc aaatgagttt      120
actggtgatc gctgccaaaa ctacgtaatg gccagcttct acaaagcgga ggagctctac      180
taa                                                                    183
```

<210> SEQ ID NO 8
<211> LENGTH: 60
<212> TYPE: PRT
<213> ORGANISM: Homo sapiens

<400> SEQUENCE: 8

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr
    50                  55                  60

<210> SEQ ID NO 9
<211> LENGTH: 210
<212> TYPE: DNA
<213> ORGANISM: Homo sapiens

<400> SEQUENCE: 9
agccatcttg tcaagtgtgc agagaaggag aaaactttct gtgtgaatgg aggcgagtgc      60
ttcatggtga agacctttc aaatccctca agatacttgt gcaagtgccc aaatgagttt     120
actggtgatc gctgccaaaa ctacgtaatg ccagcttct acaagcatct tgggattgaa     180
tttatggaga aagcggagga gctctactaa                                      210

<210> SEQ ID NO 10
<211> LENGTH: 69
<212> TYPE: PRT
<213> ORGANISM: Homo sapiens

<400> SEQUENCE: 10

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys His Leu Gly Ile Glu Phe Met Glu Lys
    50                  55                  60

Ala Glu Glu Leu Tyr
65

<210> SEQ ID NO 11
<211> LENGTH: 267
<212> TYPE: DNA
<213> ORGANISM: Homo sapiens

<400> SEQUENCE: 11
agccatcttg tcaagtgtgc agagaaggag aaaactttct gtgtgaatgg aggcgagtgc      60
ttcatggtga agacctttc aaatccctca agatacttgt gcaagtgcca acctggattc     120
actggagcga gatgtactga gaatgtgccc atgaaagtcc aaacccaaga aaagtgccca     180
aatgagttta ctggtgatcg ctgccaaaac tacgtaatgg ccagcttcta cagtacgtcc     240 actcccttc tgtctctgcc tgaatag                                          267

<210> SEQ ID NO 12
<211> LENGTH: 88
<212> TYPE: PRT
<213> ORGANISM: Homo sapiens

<400> SEQUENCE: 12

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Lys Val Gln Thr Gln Glu Lys Cys Pro Asn Glu Phe Thr
    50                  55                  60

Gly Asp Arg Cys Gln Asn Tyr Val Met Ala Ser Phe Tyr Ser Thr Ser
65                  70                  75                  80

Thr Pro Phe Leu Ser Leu Pro Glu
                85

<210> SEQ ID NO 13
<211> LENGTH: 252
<212> TYPE: DNA
<213> ORGANISM: Homo sapiens

<400> SEQUENCE: 13
agccatcttg tcaagtgtgc agagaaggag aaaactttct gtgtgaatgg aggcgagtgc      60
ttcatggtga agacctttc aaatccctca agatacttgt gcaagtgcca acctggattc     120
actggagcga gatgtactga aatgtgccc atgaaagtcc aaacccaaga aaagtgccca     180
aatgagttta ctggtgatcg ctgccaaaac tacgtaatgg ccagcttcta caaagcggag     240
gagctctact aa                                                        252

<210> SEQ ID NO 14
<211> LENGTH: 83
<212> TYPE: PRT
<213> ORGANISM: Homo sapiens

<400> SEQUENCE: 14

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Lys Val Gln Thr Gln Glu Lys Cys Pro Asn Glu Phe Thr
    50                  55                  60

Gly Asp Arg Cys Gln Asn Tyr Val Met Ala Ser Phe Tyr Lys Ala Glu
65                  70                  75                  80

Glu Leu Tyr

<210> SEQ ID NO 15
<211> LENGTH: 498
<212> TYPE: DNA
<213> ORGANISM: Homo sapiens

<400> SEQUENCE: 15
catatgttgc ctccccaatt gaaagagatg aaaagccagg aatcggctgc aggttccaaa      60
ctagtccttc ggtgtgaaac cagttctgaa tactcctctc tcagattcaa gtggttcaag     120

```
aatgggaatg aattgaatcg aaaaaacaaa ccacaaaata tcaagataca aaaaaagcca    180
gggaagtcag aacttcgcat taacaaagca tcactggctg attctggaga gtatatgtgc    240
aaagtgatca gcaaattagg aaatgacagt gcctctgcca atatcaccat cgtggaatca    300
aacgctacat ctacatccac cactgggaca agccatcttg taaaatgtgc ggagaaggag    360
aaaactttct gtgtgaatgg aggggagtgc ttcatggtga agacctttc aaacccctcg     420 agatacttgt gcaagtgccc aaatgagttt actggtgatc gctgccaaaa ctacgtaatg    480
gccagcttct acggatcc                                                  498
```

```
<210> SEQ ID NO 16
<211> LENGTH: 162
<212> TYPE: PRT
<213> ORGANISM: Homo sapiens

<400> SEQUENCE: 16

Leu Pro Pro Gln Leu Lys Glu Met Lys Ser Gln Glu Ser Ala Ala Gly
1               5                   10                  15

Ser Lys Leu Val Leu Arg Cys Glu Thr Ser Ser Glu Tyr Ser Ser Leu
            20                  25                  30

Arg Phe Lys Trp Phe Lys Asn Gly Asn Glu Leu Asn Arg Lys Asn Lys
        35                  40                  45

Pro Gln Asn Ile Lys Ile Gln Lys Lys Pro Gly Lys Ser Glu Leu Arg
    50                  55                  60

Ile Asn Lys Ala Ser Leu Ala Asp Ser Gly Glu Tyr Met Cys Lys Val
65                  70                  75                  80

Ile Ser Lys Leu Gly Asn Asp Ser Ala Ser Ala Asn Ile Thr Ile Val
                85                  90                  95

Glu Ser Asn Ala Thr Ser Thr Ser Thr Thr Gly Thr Ser His Leu Val
            100                 105                 110

Lys Cys Ala Glu Lys Glu Lys Thr Phe Cys Val Asn Gly Gly Glu Cys
        115                 120                 125

Phe Met Val Lys Asp Leu Ser Asn Pro Ser Arg Tyr Leu Cys Lys Cys
    130                 135                 140

Pro Asn Glu Phe Thr Gly Asp Arg Cys Gln Asn Tyr Val Met Ala Ser
145                 150                 155                 160

Phe Tyr

<210> SEQ ID NO 17
<211> LENGTH: 199
<212> TYPE: PRT
<213> ORGANISM: Homo sapiens

<400> SEQUENCE: 17

Met Gly Gly Ser His His His His His His Gly Met Ala Ser Met Thr
1               5                   10                  15

Gly Gly Thr Ala Asn Gly Val Gly Asp Leu Tyr Asp Asp Asp Asp Lys
            20                  25                  30

Val Pro Gly Ser Leu Pro Pro Gln Leu Lys Glu Met Lys Ser Gln Glu
        35                  40                  45

Ser Ala Ala Gly Ser Lys Leu Val Leu Arg Cys Glu Thr Ser Ser Glu
    50                  55                  60

Tyr Ser Ser Leu Arg Phe Lys Trp Phe Lys Asn Gly Asn Glu Leu Asn
65                  70                  75                  80

Arg Lys Asn Lys Pro Gln Asn Ile Lys Ile Gln Lys Lys Pro Gly Lys
```

```
                85                  90                  95
Ser Glu Leu Arg Ile Asn Lys Ala Ser Leu Ala Asp Ser Gly Glu Tyr
            100                 105                 110
Met Cys Lys Val Ile Ser Lys Leu Glu Asn Asp Ser Ala Ser Ala Asn
            115                 120                 125
Ile Thr Ile Val Glu Ser Asn Ala Thr Ser Thr Ser Thr Thr Gly Thr
    130                 135                 140
Ser His Leu Val Lys Cys Ala Glu Lys Glu Lys Thr Phe Cys Val
145                 150                 155                 160
Asn Gly Gly Glu Cys Phe Met Val Lys Asp Leu Ser Asn Pro Ser Arg
                165                 170                 175
Tyr Leu Cys Lys Cys Pro Asn Glu Phe Thr Gly Asp Arg Cys Gln Asn
            180                 185                 190
Tyr Val Met Ala Ser Phe Tyr
            195

<210> SEQ ID NO 18
<211> LENGTH: 198
<212> TYPE: DNA
<213> ORGANISM: Homo sapiens

<400> SEQUENCE: 18
catatgagcc atcttgtaaa atgtgcggag aaggagaaaa ctttctgtgt gaatggaggg      60
gagtgcttca tggtgaaaga ccttcaaac ccctcgagat acttgtgcaa gtgcccaaat     120
gagtttactg gtgatcgctg ccaaaactac gtaatggcca gcttctacaa ggcggaggag     180
ctgtaccagt aaggatcc                                                    198

<210> SEQ ID NO 19
<211> LENGTH: 82
<212> TYPE: PRT
<213> ORGANISM: Homo sapiens

<400> SEQUENCE: 19

Met Gly Ser Ser His His His His His His Ser Ser Gly Leu Val Pro
1               5                   10                  15
Arg Gly Ser His Met Ser His Leu Val Lys Cys Ala Glu Lys Glu Lys
            20                  25                  30
Thr Phe Cys Val Asn Gly Gly Glu Cys Phe Met Val Lys Asp Leu Ser
        35                  40                  45
Asn Pro Ser Arg Tyr Leu Cys Lys Cys Pro Asn Glu Phe Thr Gly Asp
    50                  55                  60
Arg Cys Gln Asn Tyr Val Met Ala Ser Phe Tyr Lys Ala Glu Glu Leu
65                  70                  75                  80
Tyr Gln

<210> SEQ ID NO 20
<211> LENGTH: 236
<212> TYPE: DNA
<213> ORGANISM: Artificial Sequence
<220> FEATURE:
<223> OTHER INFORMATION: MIS Sequence

<400> SEQUENCE: 20
cgataactag cagcatttcc tccaacgagg atcccgcagg taagaagcta caccggccag      60
tggccggggc cgataacta gcagcatttc ctccaaccag gatcccgcag gtaagaagct     120
acaccggcca gtggccgggg ccgtggagcc gggggcatcc ggtgcctgag acagaggtgc     180
```
tcaaggcagt ctccacctttt tgtctcccct ctgcagagag ccacattctg gaagtt      236

<210> SEQ ID NO 21
<211> LENGTH: 60
<212> TYPE: PRT
<213> ORGANISM: Homo sapiens

<400> SEQUENCE: 21

Ser His Leu Val Lys Cys Ala Glu Lys Glu Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr
    50                  55                  60

<210> SEQ ID NO 22
<211> LENGTH: 61
<212> TYPE: PRT
<213> ORGANISM: Homo sapiens

<400> SEQUENCE: 22

Ser His Leu Val Lys Cys Ala Glu Lys Glu Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60

<210> SEQ ID NO 23
<211> LENGTH: 1269
<212> TYPE: DNA
<213> ORGANISM: Homo sapiens

<400> SEQUENCE: 23
atgagatggc gacgcgcccc gcgccgctcc gggcgtcccg gccccgggc ccagcgcccc       60
ggctccgccg cccgctcgtc gccgccgctg ccgctgctgc cactactgct gctgctgggg      120
accgcggccc tggcgccggg ggcggcggcc ggcaacgagg cggctcccgc ggggcctcg       180
gtgtgctact cgtccccgcc cagcgtggga tcggtgcagg agctagctca gcgcgccgcg      240
gtggtgatcg agggaaaggt gcacccgcag cggcggcagc agggggcact cgacaggaag      300
gcggcggcgc cggcgggcga ggcaggggcg tgggcggcg atcgcgagcc gccagccgcg       360
ggcccacggg cgctggggcc gcccgccgag gagccgctgc tcgccgccaa cgggaccgtg      420
ccctcttggc ccaccgcccc ggtgcccagc gccggcgagc ccggggagga ggcgccctat      480
ctggtgaagg tgcaccaggt gtgggcggtg aaagccgggg gcttgaagaa ggactcgctg      540
ctcaccgtgc gcctggggac ctggggccac cccgccttcc cctcctgcgg gaggctcaag      600
gaggacagca ggtacatctt cttcatggag cccgacgcca acagcaccag ccgcgcgccg      660
gccgccttcc gagcctcttt ccccccctctg gagacgggcc ggaacctcaa gaaggaggtc      720
agccgggtgc tgtgcaagcg gtgcgccttg cctccccaat tgaaagagat gaaaagccag      780
gaatcggctg caggttccaa actagtcctt cggtgtgaaa ccagttctga atactcctct      840

```
ctcagattca agtggttcaa gaatgggaat gaattgaatc gaaaaaacaa accacaaaat    900
atcaagatac aaaaaaagcc agggaagtca gaacttcgca ttaacaaagc atcactggct    960
gattctggag agtatatgtg caaagtgatc agcaaattag gaaatgacag tgcctctgcc   1020
aatatcacca tcgtggaatc aaacgctaca tctacatcca ccactgggac aagccatctt   1080
gtaaaatgtg cggagaagga gaaaactttc tgtgtgaatg gagggagtg cttcatggtg    1140 aaagaccttt caaaccccctc gagatacttg tgcaagtgcc caaatgagtt tactggtgat   1200
cgctgccaaa actacgtaat ggccagcttc tacagtacgt ccactccctt tctgtctctg   1260
cctgaatag                                                           1269
```

<210> SEQ ID NO 24
<211> LENGTH: 422
<212> TYPE: PRT
<213> ORGANISM: Homo sapiens

<400> SEQUENCE: 24

Met Arg Trp Arg Arg Ala Pro Arg Arg Ser Gly Arg Pro Gly Arg
1               5                   10                  15

Ala Gln Arg Pro Gly Ser Ala Ala Arg Ser Ser Pro Pro Leu Pro Leu
            20                  25                  30

Leu Pro Leu Leu Leu Leu Gly Thr Ala Ala Leu Ala Pro Gly Ala
        35                  40                  45

Ala Ala Gly Asn Glu Ala Ala Pro Ala Gly Ala Ser Val Cys Tyr Ser
    50                  55                  60

Ser Pro Pro Ser Val Gly Ser Val Gln Glu Leu Ala Gln Arg Ala Ala
65                  70                  75                  80

Val Val Ile Glu Gly Lys Val His Pro Gln Arg Arg Gln Gln Gly Ala
                85                  90                  95

Leu Asp Arg Lys Ala Ala Ala Ala Gly Glu Ala Gly Ala Trp Gly
            100                 105                 110

Gly Asp Arg Glu Pro Pro Ala Ala Gly Pro Arg Ala Leu Gly Pro Pro
        115                 120                 125

Ala Glu Glu Pro Leu Leu Ala Ala Asn Gly Thr Val Pro Ser Trp Pro
    130                 135                 140

Thr Ala Pro Val Pro Ser Ala Gly Glu Pro Gly Glu Glu Ala Pro Tyr
145                 150                 155                 160

Leu Val Lys Val His Gln Val Trp Ala Val Lys Ala Gly Gly Leu Lys
                165                 170                 175

Lys Asp Ser Leu Leu Thr Val Arg Leu Gly Thr Trp Gly His Pro Ala
            180                 185                 190

Phe Pro Ser Cys Gly Arg Leu Lys Glu Asp Ser Arg Tyr Ile Phe Phe
        195                 200                 205

Met Glu Pro Asp Ala Asn Ser Thr Ser Arg Ala Pro Ala Ala Phe Arg
    210                 215                 220

Ala Ser Phe Pro Pro Leu Glu Thr Gly Arg Asn Leu Lys Lys Glu Val
225                 230                 235                 240

Ser Arg Val Leu Cys Lys Arg Cys Ala Leu Pro Pro Gln Leu Lys Glu
                245                 250                 255

Met Lys Ser Gln Glu Ser Ala Ala Gly Ser Lys Leu Val Leu Arg Cys
            260                 265                 270

Glu Thr Ser Ser Glu Tyr Ser Ser Leu Arg Phe Lys Trp Phe Lys Asn
        275                 280                 285

Gly Asn Glu Leu Asn Arg Lys Asn Lys Pro Gln Asn Ile Lys Ile Gln

```
                290                 295                 300
Lys Lys Pro Gly Lys Ser Glu Leu Arg Ile Asn Lys Ala Ser Leu Ala
305                 310                 315                 320

Asp Ser Gly Glu Tyr Met Cys Lys Val Ile Ser Lys Leu Gly Asn Asp
                325                 330                 335

Ser Ala Ser Ala Asn Ile Thr Ile Val Glu Ser Asn Ala Thr Ser Thr
            340                 345                 350

Ser Thr Thr Gly Thr Ser His Leu Val Lys Cys Ala Glu Lys Glu Lys
        355                 360                 365

Thr Phe Cys Val Asn Gly Gly Glu Cys Phe Met Val Lys Asp Leu Ser
    370                 375                 380

Asn Pro Ser Arg Tyr Leu Cys Lys Cys Pro Asn Glu Phe Thr Gly Asp
385                 390                 395                 400

Arg Cys Gln Asn Tyr Val Met Ala Ser Phe Tyr Ser Thr Ser Thr Pro
                405                 410                 415

Phe Leu Ser Leu Pro Glu
            420
```

```
<210> SEQ ID NO 25
<211> LENGTH: 11
<212> TYPE: PRT
<213> ORGANISM: Homo sapiens

<400> SEQUENCE: 25

Val Cys Leu Leu Thr Val Ala Ala Leu Pro Pro
1               5                   10

<210> SEQ ID NO 26
<211> LENGTH: 15
<212> TYPE: PRT
<213> ORGANISM: Homo sapiens

<400> SEQUENCE: 26

Ala Ser Pro Val Ser Val Gly Ser Val Gln Glu Leu Val Gln Arg
1               5                   10                  15

<210> SEQ ID NO 27
<211> LENGTH: 8
<212> TYPE: PRT
<213> ORGANISM: Homo sapiens

<400> SEQUENCE: 27

Trp Phe Val Val Ile Glu Gly Lys
1               5

<210> SEQ ID NO 28
<211> LENGTH: 9
<212> TYPE: PRT
<213> ORGANISM: Homo sapiens

<400> SEQUENCE: 28

Lys Val His Glu Val Trp Ala Ala Lys
1               5

<210> SEQ ID NO 29
<211> LENGTH: 5
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid
```

```
<400> SEQUENCE: 29

Asp Leu Leu Xaa Val
1               5

<210> SEQ ID NO 30
<211> LENGTH: 13
<212> TYPE: PRT
<213> ORGANISM: Homo sapiens
<220> FEATURE:
<221> NAME/KEY: misc_feature
<222> LOCATION: (12)..(12)
<223> OTHER INFORMATION: Xaa can be any naturally occurring amino acid

<400> SEQUENCE: 30

Leu Gly Ala Trp Gly Pro Pro Ala Phe Pro Val Xaa Tyr
1               5                   10

<210> SEQ ID NO 31
<211> LENGTH: 13
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 31

Tyr Ile Phe Phe Met Glu Pro Ala Ala Xaa Ser Ser Gly
1               5                   10

<210> SEQ ID NO 32
<211> LENGTH: 4
<212> TYPE: PRT
<213> ORGANISM: Homo sapiens

<400> SEQUENCE: 32

Leu Val Leu Arg
1

<210> SEQ ID NO 33
<211> LENGTH: 13
<212> TYPE: PRT
<213> ORGANISM: Homo sapiens
<220> FEATURE:
<221> NAME/KEY: misc_feature
<222> LOCATION: (12)..(12)
<223> OTHER INFORMATION: Xaa can be any naturally occurring amino acid

<400> SEQUENCE: 33

Lys Ala Ser Leu Ala Asp Ser Gly Glu Tyr Met Xaa Lys
1               5                   10
```

THERAPEUTIC DOSING OF A NEUREGULIN OR A SUBSEQUENCE THEREOF FOR TREATMENT OR PROPHYLAXIS OF HEART FAILURE

CROSS-REFERENCE TO RELATED APPLICATIONS

The present application is a continuation of U.S. application Ser. No. 13/904,654, filed 29 May 2013, now U.S. Pat. No. 9,198,951 issued on Dec. 1, 2015, which is a continuation of U.S. application Ser. No. 13/055,397, filed 8 Mar. 2011, now abandoned which is a national phase application under 35 U.S.C. § 371 of International Patent Application PCT Application No. PCT/US2009/004130, filed 17 Jul. 2009, which claims the benefit of U.S. Provisional Application No. 61/135,171, filed 17 Jul. 2008. The entire contents of these applications are incorporated herein by reference.

INCORPORATION OF SEQUENCE LISTING

The contents of the text file named "43509-514C01US_ST25.txt," which was created on Aug. 13, 2013 and is 26.7 KB in size, are hereby incorporated by reference in their entirety.

FIELD OF THE INVENTION

The field of the invention relates to treatment of heart failure. More specifically, the invention is directed to an improved dosing regimen whereby the therapeutic benefits of administration of a neuregulin, such as glial growth factor 2 (GGF2) or fragment thereof, are maintained and/or enhanced, while minimizing any potential side effects.

BACKGROUND OF THE INVENTION

A fundamental challenge associated with the administration of medications to patients in need thereof is the relationship between tolerability and efficacy. The therapeutic index is the range between which an efficacious dose of a substance can be administered to a patient and a dose at which undesired side effects to the patient are noted. Generally, the larger the difference between the efficacious dose and the dose at which side effects initiate, the more benign the substance and the more likely it is to be tolerated by the patient.

Heart failure, particularly congestive heart failure (CHF), one of the leading causes of death in industrialized nations. Factors that underlie congestive heart failure include high blood pressure, ischemic heart disease, exposure to cardiotoxic compounds such as the anthracycline antibiotics, radiation exposure, physical trauma and genetic defects associated with an increased risk of heart failure. Thus, CHF often results from an increased workload on the heart due to hypertension, damage to the myocardium from chronic ischemia, myocardial infarction, viral disease, chemical toxicity, radiation and other diseases such as scleroderma. These conditions result in a progressive decrease in the heart's pumping ability. Initially, the increased workload that results from high blood pressure or loss of contractile tissue induces compensatory cardiomyocyte hypertrophy and thickening of the left ventricular wall, thereby enhancing contractility and maintaining cardiac function.

Over time, however, the left ventricular chamber dilates, systolic pump function deteriorates, cardiomyocytes undergo apoptotic cell death, and myocardial function progressively deteriorates.

Neuregulins (NRGs) and NRG receptors comprise a growth factor-receptor tyrosine kinase system for cell-cell signaling that is involved in organogenesis and cell development in nerve, muscle, epithelia, and other tissues (Lemke, Mol. Cell. Neurosci. 7:247-262, 1996 and Burden et al., Neuron 18:847-855, 1997). The NRG family consists of four genes that encode numerous ligands containing epidermal growth factor (EGF)-like, immunoglobulin (Ig), and other recognizable domains. Numerous secreted and membrane-attached isoforms function as ligands in this signaling system. The receptors for NRG ligands are all members of the EGF receptor (EGFR) family, and include EGFR (or ErbB1), ErbB2, ErbB3, and ErbB4, also known as HER1 through HER4, respectively, in humans (Meyer et al., Development 124:3575-3586, 1997; Orr-Urtreger et al., Proc. Natl. Acad. Sci. USA 90: 1867-71, 1993; Marchionni et al., Nature 362:312-8, 1993; Chen et al., J. Comp. Neurol. 349:389-400, 1994; Corfas et al., Neuron 14:103-115, 1995; Meyer et al., Proc. Natl. Acad. Sci. USA 91:1064-1068, 1994; and Pinkas-Kramarski et al., Oncogene 15:2803-2815, 1997).

The four NRG genes, NRG-1, NRG-2, NRG-3, and NRG-4, map to distinct chromosomal loci (Pinkas-Kramarski et al., Proc. Natl. Acad. Sci. USA 91:9387-91, 1994; Carraway et al., Nature 387:512-516, 1997; Chang et al., Nature 387:509-511, 1997; and Zhang et al., Proc. Natl. Acad. Sci. USA 94:9562-9567, 1997), and collectively encode a diverse array of NRG proteins. The gene products of NRG-1, for example, comprise a group of approximately 15 distinct structurally-related isoforms (Lemke, Mol. Cell. Neurosci. 7:247-262, 1996 and Peles and Yarden, BioEssays 15:815-824, 1993). The first-identified isoforms of NRG-1 included Neu Differentiation Factor (NDF; Peles et al., Cell 69, 205-216, 1992 and Wen et al., Cell 69, 559-572, 1992), heregulin (HRG; Holmes et al., Science 256:1205-1210, 1992), Acetylcholine Receptor Inducing Activity (ARIA; Falls et al., Cell 72:801-815, 1993), and the glial growth factors GGF1, GGF2, and GGF3 (Marchionni et al. Nature 362:312-8, 1993).

The NRG-2 gene was identified by homology cloning (Chang et al., Nature 387:509-512, 1997; Carraway et al., Nature 387:512-516, 1997; and Higashiyama et al., J. Biochem. 122:675-680, 1997) and through genomic approaches (Busfield et al., Mol. Cell. Biol. 17:4007-4014, 1997). NRG-2 cDNAs are also known as Neural- and Thymus-Derived Activator of ErbB Kinases (NTAK; Genbank Accession No. AB005060), Divergent of Neuregulin (Don-1), and Cerebellum-Derived Growth Factor (CDGF; PCT application WO 97/09425). Experimental evidence shows that cells expressing ErbB4 or the ErbB2/ErbB4 combination are likely to show a particularly robust response to NRG-2 (Pinkas-Kramarski et al., Mol. Cell. Biol. 18:6090-6101, 1998). The NRG-3 gene product (Zhang et al., supra) is also known to bind and activate ErbB4 receptors (Hijazi et al., Int. J. Oncol. 13:1061-1067, 1998).

An EGF-like domain is present at the core of all forms of NRGs, and is required for binding and activating ErbB receptors. Deduced amino acid sequences of the EGF-like domains encoded in the three genes are approximately 30-40% identical (pairwise comparisons). Further, there appear to be at least two sub-forms of EGF-like domains in NRG-1 and NRG-2, which may confer different bioactivities and tissue-specific potencies.

Cellular responses to NRGs are mediated through the NRG receptor tyrosine kinases EGFR, ErbB2, ErbB3, and ErbB4 of the epidermal growth factor receptor family. High-affinity binding of all NRGs is mediated principally via either ErbB3 or ErbB4. Binding of NRG ligands leads to dimerization with other ErbB subunits and transactivation by phosphorylation on specific tyrosine residues. In certain experimental settings, nearly all combinations of ErbB receptors appear to be capable of forming dimers in response to the binding of NRG-1 isoforms. However, it appears that ErbB2 is a preferred dimerization partner that may play an important role in stabilizing the ligand-receptor complex. ErbB2 does not bind ligand on its own, but must be heterologously paired with one of the other receptor subtypes. ErbB3 does possess tyrosine kinase activity, but is a target for phosphorylation by the other receptors. Expression of NRG-1, ErbB2, and ErbB4 is known to be necessary for trabeculation of the ventricular myocardium during mouse development.

Neuregulins stimulate compensatory hypertrophic growth and inhibit apoptosis of myocardiocytes subjected to physiological stress. In accordance with these observations, administration of a neuregulin is useful for preventing, minimizing, or reversing congestive heart disease resulting from underlying factors such as hypertension, ischemic heart disease, and cardiotoxicity. See, e.g., U.S. Pat. No. 6,635,249, which is incorporated herein in its entirety.

In view of the high prevalence of heart failure in the general population, there continues to be an unmet need to prevent or minimize progression of this disease, such as by inhibiting loss of cardiac function or by improving cardiac function

SUMMARY OF THE INVENTION

The present invention comprises a method for treating or preventing heart failure in a mammal. The method is based on the surprising observation that therapeutic benefits of a peptide that comprises an epidermal growth factor-like (EGF-like) domain can be achieved by dosing regimens for neuregulin administration that do not maintain steady-state such as by administering a therapeutically effective amount of the peptide to a mammal at administration intervals of at or over 48, 72, 96 or more hours. Accordingly, the present method calls for intermittent or discontinuous administration (every 48 to 96 hours, or even longer intervals) of a peptide that contains an EGF-like domain to the mammal, wherein the EGF-like domain is encoded by a neuregulin gene, and wherein administration of the peptide is in an amount effective to treat or prevent heart failure in the mammal. Dosing regimens for neuregulin administration that do not maintain steady-state concentrations are equally as effective as more frequent dosing regimens, yet without the inconvenience, costs or side effects that can result from more frequent administration. As used herein the term intermittent or discontinuous administration includes a regimen for dosing on intervals of at least 48 hours, 72 hours, 96 hours, 1 day, 2 days, 3 days, 4 days, 5 days, 6 days, 7 days, 8 days, 9 days, 10 days, 11 days, 12 days, 13 days, 14 days 1 week, 2 weeks, 4 weeks, 1 month, 2 months, 3 months, 4 months, or any combination or increment thereof so long as the interval/regimen is at least 48 hours, 72 hours, 96 hours, 1 day, 2 days, 3 days, 4 days, 5 days, 6 days, 7 days, 8 days, 9 days, 10 days, 11 days, 12 days, 13 days, 14 days 1 week, 2 weeks, 4 weeks, 1 month, 2 months, 3 months, 4 months. As used herein the term intermittent or discontinuous administration includes a regimen for dosing on intervals of not less than 48 hours, 72 hours, 96 hours, 1 day, 2 days, 3 days, 4 days, 5 days, 6 days, 7 days, 8 days, 9 days, 10 days, 11 days, 12 days, 13 days, 14 days 1 week, 2 weeks, 4 weeks, 1 month, 2 months, 3 months, 4 months, or any combination or increment thereof so long as the interval/regimen is not less than 48 hours, 72 hours, 96 hours, 1 day, 2 days, 3 days, 4 days, 5 days, 6 days, 7 days, 8 days, 9 days, 10 days, 11 days, 12 days, 13 days, 14 days 1 week, 2 weeks, 4 weeks, 1 month, 2 months, 3 months, 4 months.

In accordance with the present invention, intermittent or discontinuous administration) of a peptide that contains an EGF-like domain to the mammal, wherein the EGF-like domain is encoded by a neuregulin gene, is directed to achieving a dosing regimen wherein narrow steady-state concentrations of the administered peptide are not maintained, thereby reducing the probability that the mammal will experience untoward side effects that may result from maintaining supraphysiological levels of the administered peptide over a prolonged duration. For example, side effects associated with supraphysiological levels of exogenously administered NRG include nerve sheath hyperplasia, mammary hyperplasia, renal nephropathy, hypospermia, hepatic enzyme elevation, heart valve changes and skin changes at the injection site.

In a preferred embodiment, the present invention is directed to an intermittent dosing regimen that elicts or permits fluctuations in the serum levels of the peptide comprising an EGF-like domain encoded by a neuregulin gene and thus reduces the potential for adverse side effects associated with more frequent administration of the peptide. The intermittent dosing regimen of the present invention thus confers therapeutic advantage to the mammal, but does not maintain steady state therapeutic levels of the peptide comprising an EGF-like domain encoded by a neuregulin gene. As appreciated by those of ordinary skill in the art, there are a various embodiments of the invention to obtain the intermittent dosing; the benefits of these embodiments can be stated in various ways for example, said administering does not maintain steady state therapeutic levels of said peptide, the administering reduces potential for adverse side effects associated with administration of NRG peptide more frequently, and the like.

In particular embodiments of the invention, the neuregulin may be the gene, gene product or respective subsequence or fragment thereof comprising, consisting essentially of or consisting of: NRG-1, NRG-2, NRG-3 or NRG-4. In a preferred embodiment an NRG subsequence or fragment of the invention comprises an epidermal growth factor-like (EGF-like) domain or a homologue thereof. As appreciated by person s of ordinary skill in the art, a peptide homologue to an EGF-like domain peptide is determined by finding structural homology or by the homologue peptide performing as a EGF-like peptide does in functional assays such as by binding and activating ErbB receptors. Preferably the fragment is at least 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 amino acids long. A neuregulin peptide of the invention may, in turn, be encoded by any one of these neuregulin genes (or subsequence thereof). In a more particular embodiment, the peptide used in the method is recombinant human GGF2 or a fragment or subsequence thereof. See FIGS. 8A-8D for the amino and nucleic acid sequences of full length human GGF2.

In an aspect of the invention, suitable mammals include, but are not limited to, mice, rats, rabbits, dogs, monkeys or pigs. In one embodiment of the invention, the mammal is a human.

In other embodiments of the invention, the heart failure may result from hypertension, ischemic heart disease, exposure to a cardiotoxic compound (e.g., cocaine, alcohol, an anti-ErbB2 antibody or anti-HER antibody, such as HERCEPTIN®, or an anthracycline antibiotic, such as doxorubicin or daunomycin), myocarditis, thyroid disease, viral infection, gingivitis, drug abuse, alcohol abuse, periocarditis, atherosclerosis, vascular disease, hypertrophic cardiomyopathy, acute myocardial infarction or previous myocardial infarction, left ventricular systolic dysfunction, coronary bypass surgery, starvation, radiation exposure, an eating disorder, or a genetic defect.

In another embodiment of the invention, an anti-ErbB2 or anti-HER2 antibody, such as HERCEPTIN®, is administered to the mammal before, during, or after anthracycline administration.

In other embodiments of the invention, the peptide is administered prior to exposure to a cardiotoxic compound, during exposure to said cardiotoxic compound, or after exposure to said cardiotoxic compound; the peptide is administered prior to or after the diagnosis of congestive heart failure in said mammal. A method of the invention can take place after the subject mammal has undergone compensatory cardiac hypertrophy; a method of the invention comprises that the outcome of the method is to maintain left ventricular hypertrophy or to prevent progression of myocardial thinning, or inhibiting cardiomyocyte apoptosis. In a method of the invention, the peptide can comprising, consisting essentially of, or consisting of an EGF-like domain encoded by a neuregulin gene. A peptide of the invention is administered before, during, or after exposure to a cardiotoxic compound. In another embodiment, the peptide containing the EGF-like domain is administered during two, or all three, of these periods. In accordance with the present invention, the peptide containing an EGF-like domain encoded by a neuregulin gene is administered at intervals of every 48 to 96 hours. In one embodiment of the present invention, the peptide containing an EGF-like domain encoded by a neuregulin gene is GGF2. In still other embodiments of the invention, the peptide is administered either prior to or after the diagnosis of congestive heart failure in the mammal. In yet another embodiment of the invention, the peptide is administered to a mammal that has undergone compensatory cardiac hypertrophy. In other particular embodiments of the invention, administration of the peptide maintains left ventricular hypertrophy, prevents progression of myocardial thinning, and/or inhibits cardiomyocyte apoptosis.

Embodiments of the invention include the following: A method for treating heart failure in a mammal, said method comprising administering an exogenous peptide comprising an epidermal growth factor-like (EGF-like) domain to said mammal, wherein said administering at said intervals reduces adverse side effects associated with administration of said exogenous peptide in said mammal. A method for treating heart failure in a mammal, said method comprising administering an exogenous peptide comprising an epidermal growth factor-like (EGF-like) domain to said mammal, wherein said EGF-like domain is encoded by the neuregulin (NRG)-1 gene, and said exogenous peptide is administered in a therapeutically effective amount to treat heart failure in said mammal at intervals of at least 48 hours, wherein said administering at said intervals does not maintain steady state levels of said exogenous peptide in said mammal. A method for treating heart failure in a mammal, said method comprising administering an exogenous peptide comprising an epidermal growth factor-like (EGF-like) domain or homologue thereof to said mammal, and said exogenous peptide is administered in a therapeutically effective amount to treat heart failure in said mammal at intervals of at least or not less than 48 hours, wherein said administering at said intervals permits intradose fluctuation of serum concentrations of said exogenous peptide to baseline or pre-administration levels in said mammal.

As used herein, the term adverse or deleterious side effect refers to an unintended and undesirable consequence of a medical treatment. With respect to the present invention, an adverse or deleterious side effect resulting from administration of an exogenous peptide may include any one or more of the following: nerve sheath hyperplasia, mammary hyperplasia, renal nephropathy, and skin changes at the injection site.

As used herein, the term "intradose fluctuation of serum concentrations of said exogenous peptide to pre-administration levels in said mammal" refers to the difference between serum concentration levels before administration of a dose of an exogenous peptide.

As used herein, the term "steady state levels" refers to a level(s) of an exogenous agent (e.g., a peptide) that is sufficient to achieve equilibration (within a range of fluctuation between succeeding doses) between administration and elimination. "Maintaining steady state therapeutic levels" refers to sustaining the concentration of an exogenous agent at a level sufficient to confer therapeutic benefit to a subject or patient.

BRIEF DESCRIPTION OF THE DRAWINGS

FIGS. 8A-D show the nucleic and amino acid sequences of full length GGF2. The nucleic acid sequence is designated SEQ ID NO: 1 and the amino acid sequence is designated SEQ ID NO: 2. GGF2 variant sequences are identified as follows: GGF-II 09 (SEQ ID NO: 25), GGF-II 08 (SEQ ID NO: 26), GGF-II 04 (SEQ ID NO: 27), GGF-II 01 and 11 (SEQ ID NO: 28), GGF-II 10 (SEQ ID NO: 29), GGF-II 03 (SEQ ID NO: 30), GGF-II 02 (SEQ ID NO: 31), GGF-II 06 (SEQ ID NO: 32), GGF-II 12 (SEQ ID NO: 33).

FIG. 9 shows the nucleic and amino acid sequences of epidermal growth factor-like (EGFL) domain 1. The nucleic acid sequence of EGFL domain 1 is designated herein SEQ ID NO: 3 and the amino acid sequence of EGFL domain 1 is designated herein SEQ ID NO: 4.

FIG. 10 shows the nucleic and amino acid sequences of epidermal growth factor-like (EGFL) domain 2. The nucleic acid sequence of EGFL domain 2 is designated herein SEQ ID NO: 5 and the amino acid sequence of EGFL, domain 2 is designated herein SEQ ID NO: 6.

FIG. 11 shows the nucleic and amino acid sequences of epidermal growth factor-like (EGFL) domain 3. The nucleic acid sequence of EGFL domain 3 is designated herein SEQ ID NO: 7 and the amino acid sequence of EGFL, domain 3 is designated herein SEQ ID NO: 8.

FIG. 12 shows the nucleic and amino acid sequences of epidermal growth factor-like (EGFL) domain 4. The nucleic acid sequence of EGFL domain 4 is designated herein SEQ ID NO: 9 and the amino acid sequence of EGFL domain 4 is designated herein SEQ ID NO: 10.

FIG. 13 shows the nucleic and amino acid sequences of epidermal growth factor-like (EGFL) domain 5. The nucleic acid sequence of EGFL domain 5 is designated herein SEQ ID NO: 11 and the amino acid sequence of EGFL domain 5 is designated herein SEQ ID NO: 12.

FIG. 14 shows the nucleic and amino acid sequences of epidermal growth factor-like (EGFL) domain 6. The nucleic acid sequence of EGFL domain 6 is designated herein SEQ ID NO: 13 and the amino acid sequence of EGFL domain 6 is designated herein SEQ ID NO: 14.

FIG. 15 shows the amino acid sequence of a polypeptide comprising an epidermal growth factor-like (EGFL) domain, which is designated herein SEQ ID NO: 21.

FIG. 16 shows schematic diagrams of expression vectors pSV-AHSG and pCMGGF2.

DETAILED DESCRIPTION OF THE INVENTION

Figure 1:
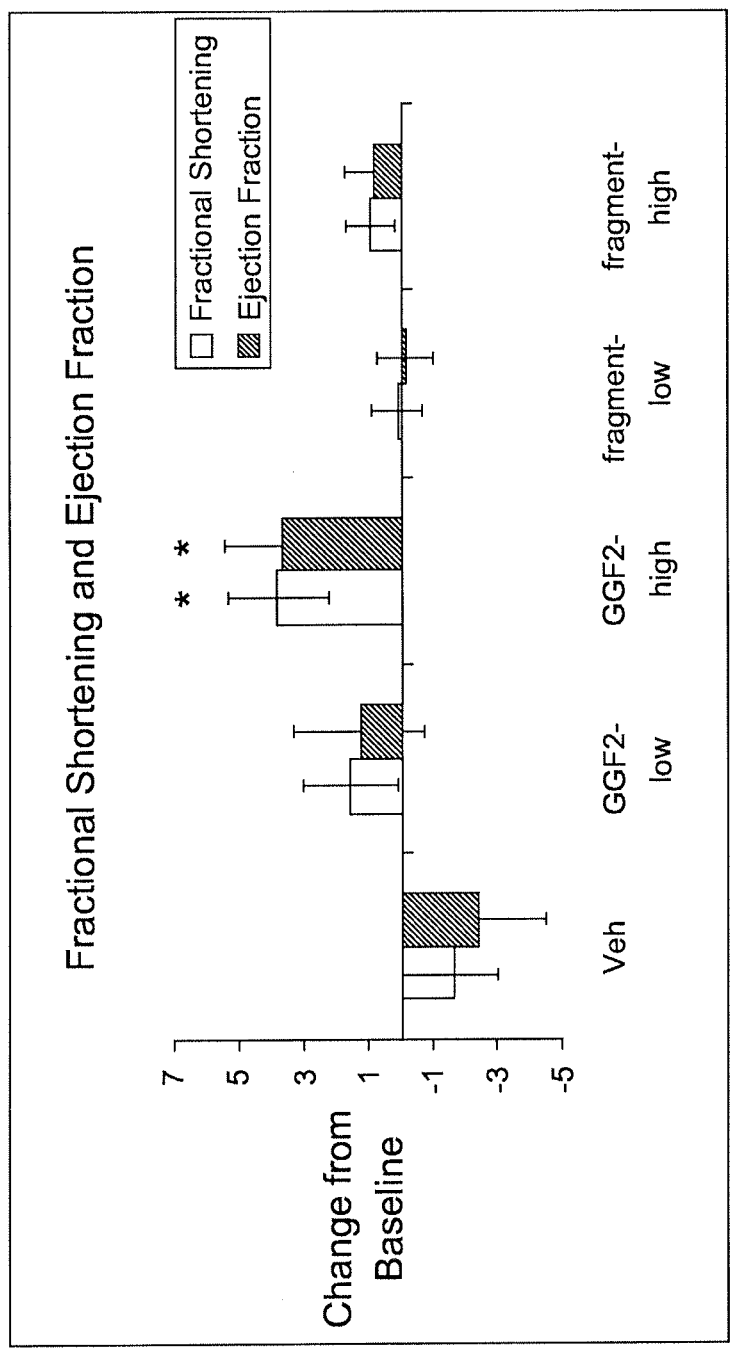
FIG. 1 shows a histogram depicting cardiac function as exemplified by changes in Ejection Fraction and Fractional Shortening. As indicated, rats were treated with GGF2 at 0.625 mg/kg or an equimolar amount of an EGF-like fragment (fragment; EGF-id) intravenously (iv) everyday (q day).
Figure 2:
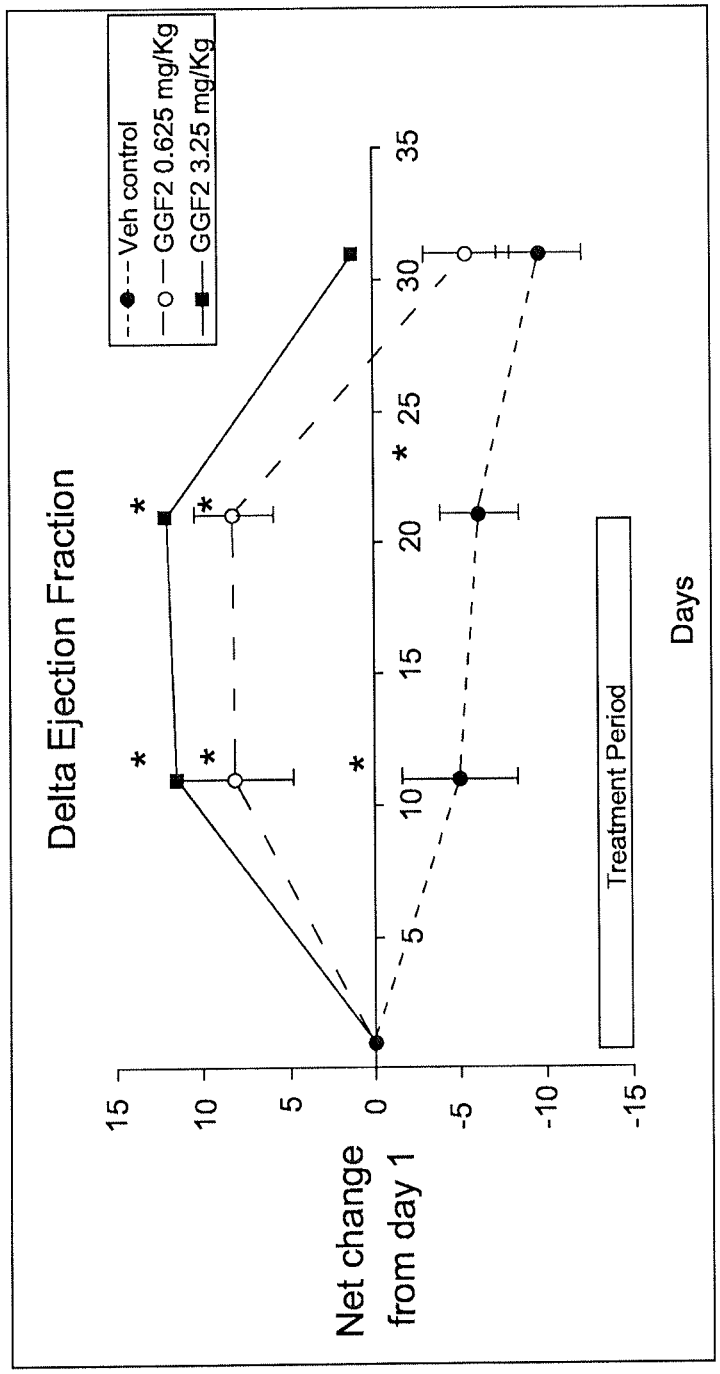
FIG. 2 shows a line graph depicting cardiac function as revealed by changes in Ejection Fraction and Fractional Shortening. As indicated, rats were treated with GGF2 at 0.625 mg/kg or 3.25 mg/kg iv q day.
Figure 3:
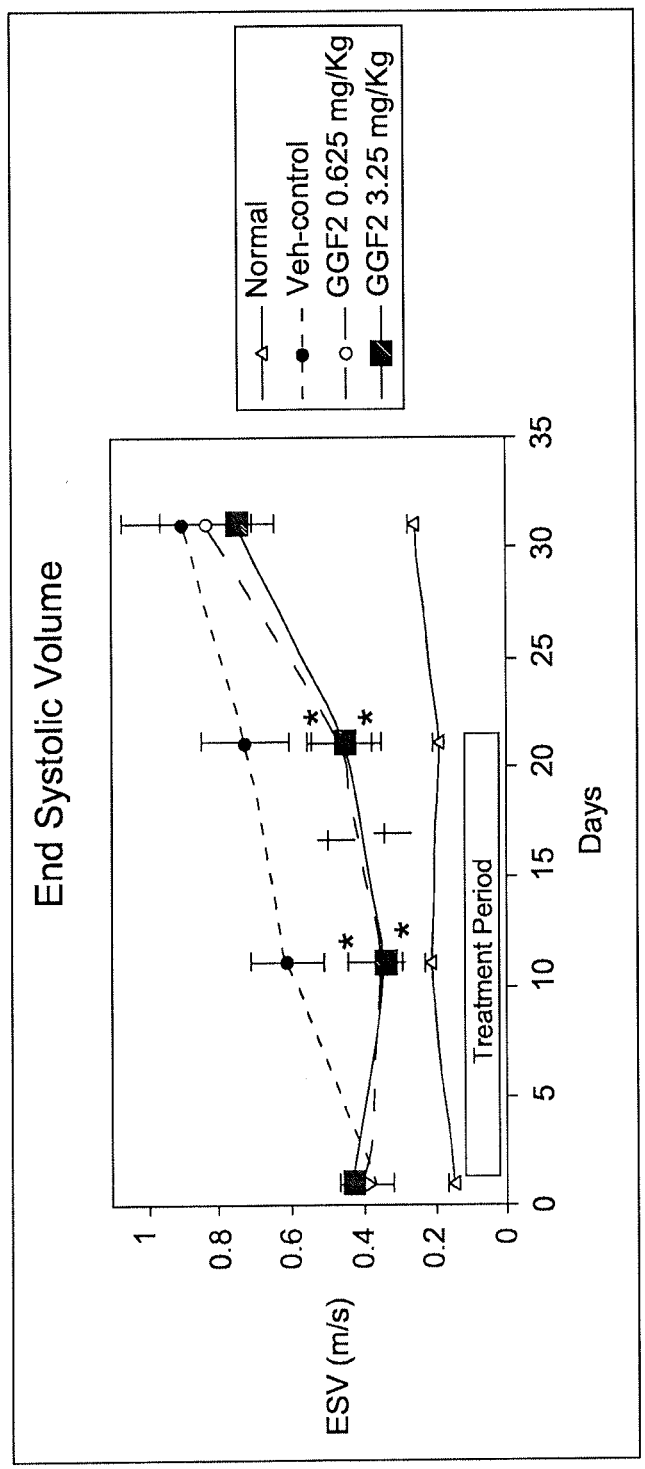
FIG. 3 shows a line graph depicting cardiac function as revealed by significant improvement in end systolic volume during the treatment period. As indicated, rats were treated with GGF2 at 0.625 mg/kg or 3.25 mg/kg iv q day.
Figure 4:
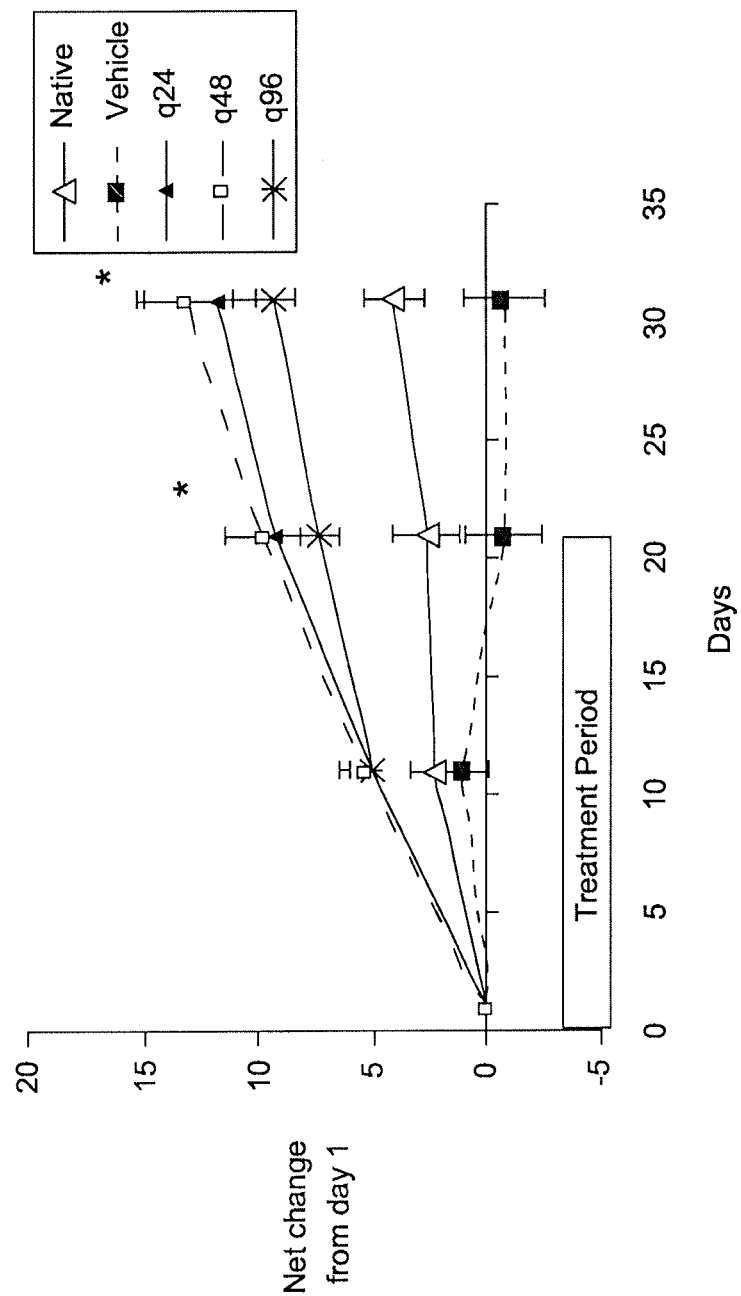
FIG. 4 shows a line graph depicting cardiac function as revealed by changes in Ejection Fraction and Fractional Shortening. As indicated, rats were treated with GGF2 3.25 mg/kg intravenously (iv) q24, 48 or 96 hours.
Figure 5:
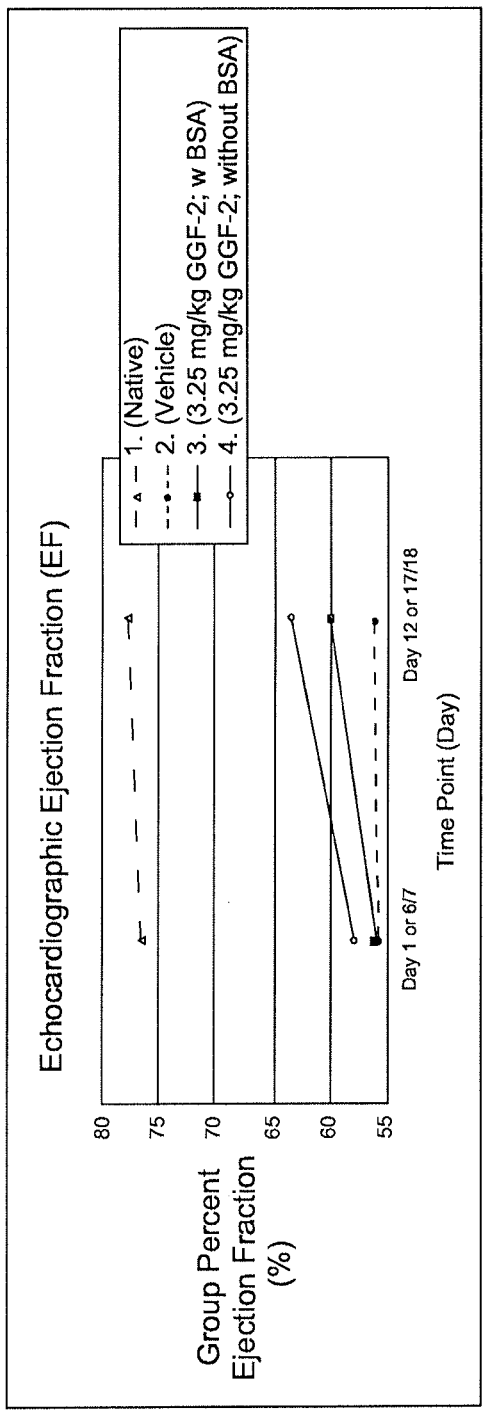
FIG. 5 shows a line graph depicting cardiac function as revealed by changes in the echocardiographic ejection fraction. As indicated, rats were treated with vehicle or GGF2 3.25 mg/kg intravenously (iv), with or without BSA.

The present inventors made the surprising discovery that discontinuous or intermittent administration of a neuregulin at appropriately spaced time intervals delivers a therapeutically effective amount of the neuregulin to a patient in need thereof and such a treatment regimen is useful for preventing, prophylaxing, ameliorating, minimizing, treating or reversing heart disease, such as congestive heart failure.

Despite conventional wisdom and development practice pertaining to designing dosing regimens to maintain the most narrow range steady state concentrations, the present inventors demonstrate herein that dosing regimens for neuregulin administration that do not maintain narrow steady-state concentrations are equally as effective as more frequent dosing regimens. Indeed, the present inventors have shown that neuregulin treatment of heart failure with dosing intervals of at least 48 hours, 72 hours, 96 hours, 1 day, 2 days, 3 days, 4 days, 5 days, 6 days, 7 days, 8 days, 9 days, 10 days, 11 days, 12 days, 13 days, 14 days 1 week, 2 weeks, 4 weeks, 1 month, 2 months, 3 months, 4 months, or any combination or increment thereof so long as the interval/regimen is at least 48 hours is as effective as daily dosing.

In order to evaluate the pharmacokinetics of exogenous NRG, the present inventors have shown that the half-life of neuregulin when delivered intravenously is 4 to 8 hours and when delivered subcutaneously is 11-15 hours. See, e.g., Tables 1 and 2 and FIGS. 6 and 7. Dosing at regimens as infrequent as every fourth day would, therefore, not maintain any detectable levels for at least three days between doses. Based on these findings, prior to the present invention, one would not have predicted that such peak/trough ratios would correlate with consistent therapeutic benefit. It is, noteworthy that compounds with a half-life of this order are generally administered in accordance with a frequent dosing regimen (e.g., daily or multiple daily doses). Indeed, based on pharmacokinetic data available for GGF2, traditional development would predict that optimal treatment would involve daily subcutaneous dosing.

In keeping with conventional wisdom and development practice, other medical treatments for CHF are typically administered on at least a daily basis. The periodicity of such a regimen is thought to be required because CHF is a chronic condition, commonly caused by impaired contraction and/or relaxation of the heart, rather than an acute condition. In persons with a weak heart leading to impaired relaxation and CHF, medical treatments include drugs that block formation or action of specific neurohormones (e.g. angiotensin converting enzyme inhibitors (ACE-inhibitors), angiotensin receptor antagonists (ARBs), aldosterone antagonists and beta-adrenergic receptor blockers). These and other medications are now standard of care in chronic CHF as they have been demonstrated to result in improved symptoms, life expectancy and/or a reduction in hospitalizations. In the setting of acute exacerbation or chronic symptoms, patients are often treated with inotropes (e.g. dobutamine, digoxin) to enhance cardiac contractility, along with vasodilators (e.g. nitrates, nesiritide) and/or diuretics (e.g. furosemide) to reduce congestion. Patients with hypertension and congestive heart failure are treated with one or more antihypertensive agent such as beta-blockers, ACE-inhibitors and ARBs, nitrates (isosorbide dinitrate), hydralazine, and calcium channel blockers.

Thus, despite typical practice with respect to treatment of CHF, the present inventors have demonstrated that a novel dosing regimen results in effective treatment of CHF, while avoiding undesirable side-effects. Although not wishing to be bound by theory, it is likely that such neuregulin treatment strengthens the pumping ability of the heart by stimulating cardiomyocyte hypertrophy, and partially or completely inhibits further deterioration of the heart by suppressing cardiomyocyte apoptosis.

By way of additional background, the basic principle of dosing is to determine an effective circulating concentration and design a dosing regimen to maintain those levels. Pharmacokinetic (PK) and pharmacodynamic (PD) studies are combined to predict a dosing regimen that will maintain a steady-state level of a particular drug. The typical plan is to minimize the difference between the Cmax and Cmin and thereby reduce side-effects.

Drugs are described by their 'therapeutic index' which is a ratio of the toxic dose or circulating levels divided by the effective dose or circulating concentrations. When the therapeutic index is large there Is a wide safety range where an effective dose can be given without approaching toxic levels. When untoward effects result at concentrations too close to the effective concentrations the therapeutic index is described as narrow and the drug is difficult to administer safely.

While developing dosing regimens one combines the PK/PD data with knowledge of the therapeutic index to design a dose and frequency of administration such that the compound is maintained at a concentration in a patient (e.g., a human) such that it is above the effective concentration and below the toxic concentration. If an effective concentration of the drug cannot be maintained without inducing unsafe effects, the drug will fail during development. Additional commentary pertaining to drug development can be found in a variety of references, including: Pharmacokinetics in Drug Development: Clinical Study Design and Analysis (2004, Peter Bonate and Danny Howard, eds.), which is incorporated herein in its entirety.

Neuregulins are growth factors related to epidermal growth factors that bind to erbB receptors. They have been shown to improve cardiac function in multiple models of heart failure, cardiotoxicity and ischemia. They have also been shown to protect the nervous system in models of stroke, spinal cord injury, nerve agent exposure, peripheral nerve damage and chemotoxicity.

Maintaining supranormal levels of exogenously supplied neuregulins has, however, been shown to have untoward effects including nerve sheath hyperplasia, mammary hyperplasia and renal nephropathy. These effects were observed following daily subcutaneous administration of neuregulin. See, e.g., Table 10.

As set forth herein, subcutaneous administration was explored due to the prolonged half-life compared with Intravenous administration and the initial belief that maintaining constant levels of ligand would be advantageous. Developing dosing regimens to reduce these effects would significantly enhance the ability of neuregulins to be utilized as therapeutics and it is toward this end that the present invention is directed. Demonstrating that less frequent dosing that does not maintain constant levels is also effective enables this development.

Neuregulins: As indicated above, peptides encoded by the NRG-1, NRG-2, NRG-3 and NRG-4 genes possess EGF-like domains that allow them to bind to and activate ErbB receptors. Holmes et al. (Science 256:1205-1210, 1992) have shown that the EGF-like domain alone is sufficient to bind and activate the p185erbB2 receptor. Accordingly, any peptide product encoded by the NRG-1, NRG-2, or NRG-3 gene, or any neuregulin-like peptide, e.g., a peptide having an EGF-like domain encoded by a neuregulin gene or cDNA (e.g., an EGF-like domain containing the NRG-1 peptide subdomains C-C/D or C-C/D', as described in U.S. Pat. Nos. 5,530,109, 5,716,930, and 7,037,888; or an EGF-like domain as disclosed in WO 97/09425) may be used in the methods of the invention to prevent or treat congestive heart failure. The contents of each of U.S. Pat. Nos. 5,530,109; 5,716,930; 7,037,888; and WO 97/09425 is incorporated herein in its entirety.

Risk Factors: Risk factors that increase the likelihood of an individual's developing congestive heart failure are well known. These include, and are not limited to, smoking, obesity, high blood pressure, ischemic heart disease, vascular disease, coronary bypass surgery, myocardial infarction, left ventricular systolic dysfunction, exposure to cardiotoxic compounds (alcohol, drugs such as cocaine, and anthracycline antibiotics such as doxorubicin, and daunorubicin), viral infection, pericarditis, myocarditis, gingivitis, thyroid disease, radiation exposure, genetic defects known to increase the risk of heart failure (such as those described in Bachinski and Roberts, Cardiol. Clin. 16:603-610, 1998; Siu et al., Circulation 8:1022-1026, 1999; and Arbustini et al., Heart 80:548-558, 1998), starvation, eating disorders such as anorexia and bulimia, family history of heart failure, and myocardial hypertrophy.

In accordance with the present invention, neuregulins may be administered intermittently to achieve prophylaxis such as by preventing or decreasing the rate of congestive heart disease progression in those identified as being at risk. For example, neuregulin administration to a patient in early compensatory hypertrophy permits maintenance of the hypertrophic state and prevents the progression to heart failure. In addition, those identified to be at risk may be given cardioprotective neuregulin treatment prior to the development of compensatory hypertrophy.

Neuregulin administration to cancer patients prior to and during anthracycline chemotherapy or anthracycline/anti-ErbB2 (anti-HER2) antibody (e.g., HERCEPTIN®) combination therapy can prevent a patient's cardiomyocytes from undergoing apoptosis, thereby preserving cardiac function. Patients who have already suffered cardiomyocyte loss also derive benefit from neuregulin treatment, because the remaining myocardial tissue responds to neuregulin exposure by displaying hypertrophic growth and increased contractility.

Therapy: Neuregulins and peptides containing EGF-like domains encoded by neuregulin genes may be administered to patients or experimental animals with a pharmaceutically-acceptable diluent, carrier, or excipient. Compositions of the invention can be provided in unit dosage form.

Conventional pharmaceutical practice is employed to provide suitable formulations or compositions, and to administer such compositions to patients or experimental animals. Although intravenous administration is preferred, any appropriate route of administration may be employed, for example, parenteral, subcutaneous, intramuscular, transdermal, intracardiac, intraperitoneal, intranasal, aerosol, oral, or topical (e.g., by applying an adhesive patch carrying a formulation capable of crossing the dermis and entering the bloodstream) administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Other potentially useful parenteral delivery systems for administering molecules of the invention include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

With respect to intravenous injections, dose levels range from about 0.001 mg/kg, 0.01 mg/kg to at least 10 mg/kg, in regular time intervals of from at least about every 24, 36, 48 hours to about every 96 hours and especially every 48, 72, or 96 hours or more as set forth herein. In a particular embodiment, intravenous injection dose levels range from about 0.1 mg/kg to about 10 mg/kg, in regular time intervals of from about every 48 hours to about every 96 hours and especially every 48, 72, or 96 hours or more as set forth herein. In another particular embodiment, intravenous injection dose levels range from about 1 mg/kg to about 10 mg/kg, in regular time intervals of from about every 48 hours to about every 96 hours and especially every 48, 72, or 96 hours or more as set forth herein. In yet another particular embodiment, intravenous injection dose levels range from about 0.01 mg/kg to about 1 mg/kg, in regular time intervals of from about every 48 hours to about every 96 hours and especially every 48, 72, or 96 hour or more as set forth hereins. In yet another particular embodiment, intravenous injection dose levels range from about 0.1 mg/kg to about 1 mg/kg, in regular time intervals of from about every 48 hours to about every 96 hours and especially every 48, 72, or 96 hours or more as set forth herein.

With respect to subcutaneous injections, dose levels range from about 0.01 mg/kg to at least 10 mg/kg, in regular time intervals of from about every 48 hours to about every 96 hours and especially every 48, 72, or 96 hours or more as set forth herein. In a particular embodiment, injection dose levels range from about 0.1 mg/kg to about 10 mg/kg, in regular time intervals of from about every 48 hours to about every 96 hours or more as set forth herein, and especially every 48, 72, or 96 hours. In another particular embodiment, injection dose levels range from about 1 mg/kg to about 10 mg/kg, in regular time intervals of from about every 48 hours to about every 96 hours or more as set forth herein, and especially every 48, 72, or 96 hours.

In yet another particular embodiment, injection dose levels range from about 0.01 mg/kg to about 1 mg/kg, in regular time intervals of from about every 48 hours to about every 96 hours or more as set forth herein, and especially every 48, 72, or 96 hours. In yet another particular embodiment, injection dose levels range from about 0.1 mg/kg to about 1 mg/kg, in regular time intervals of from about every 48 hours to about every 96 hours or more as set forth herein, and especially every 48, 72, or 96 hours.

Transdermal doses are generally selected to provide similar or lower blood levels than are achieved using injection doses.

The compounds of the invention can be administered as the sole active agent or they can be administered in combination with other agents, including other compounds that demonstrate the same or a similar therapeutic activity and that are determined to be safe and efficacious for such combined administration. Other such compounds used for the treatment of CHF include brain natriuretic peptide (BNP), drugs that block formation or action of specific neurohormones (e.g. angiotensin converting enzyme inhibitors (ACE-inhibitors), angiotensin receptor antagonists (ARBs), aldosterone antagonists and beta-adrenergic receptor blockers), inotropes (e.g. dobutamine, digoxin) to enhance cardiac contractility, vasodilators (e.g. nitrates, nesiritide) and/or diuretics (e.g. furosemide) to reduce congestion, and one or more antihypertensive agents such as beta-blockers, ACE-inhibitors and ARBs, nitrates (isosorbide dinitrate), hydralazine, and calcium channel blockers.

As indicated above, medical intervention involving drug treatment calls for the selection of an appropriate drug and its delivery at an adequate dosage regimen. An adequate dosage regimen involves a sufficient dose, route, frequency, and duration of treatment. The ultimate objective of drug therapy is the acquisition of optimal drug concentrations at the site of action so as to enable the treated patient to overcome the pathologic process for which treatment is necessitated. Broadly speaking, basic knowledge of the principles of drug disposition facilitates the selection of appropriate dosage regimens. Therapeutic drug monitoring (TDM) can, however, be used in this context as a supplemental tool to assist an attending physician in determining effective and safe dosage regimens of selected drugs for medical therapy of individual patients.

Target Concentration and Therapeutic Window: The definition of optimal drug concentration varies depending on the pharmacodynamic features of the particular drug. Optimal therapy for time-dependent antibiotics like penicillin, for example, is related to achieving peak concentration to MIC (minimum inhibitory concentration) ratios of 2-4 and a time above the MIC equal to 75% of the dose interval. For concentration-dependent antibiotics like gentamicin, for example, efficacy is related to obtaining peak concentration to MIC ratios of about 8-10. Irrespective of the nuances associated with administration of a particular drug, drug therapy aims to achieve target plasma concentrations (which often reflect the concentrations at the site of action) within the limits of a "therapeutic window", which has been previously determined based on the pharmacokinetic, pharmacodynamic and toxicity profiles of the drug in the target species. The width of this window varies for different drugs and species. When the difference between the minimum efficacious concentration and the minimum toxic concentration is small (2 to 4-fold), the therapeutic window is referred to as narrow. In contrast, when there is a large difference between the effective and toxic concentration, the drug is viewed as having a wide therapeutic window. An example of a drug with a narrow therapeutic window is digoxin, in which the difference between the average effective and toxic concentrations is 2 or 3-fold. Amoxicillin, on the other hand, has a wide therapeutic range and overdosing of a patient is not generally associated with toxicity problems.

Variability in Drug Responsiveness: Pronounced variability among healthy subjects of the same species with respect drug responsiveness is common. Moreover, disease states have the potential to affect organ systems and functions (e.g., kidney, liver, water content) that may in turn affect drug responsiveness. This, in turn, contributes to increased differentials in drug responsiveness in sick individuals to whom the drug is administered. Yet another relevant issue relates to administration of more than one drug at a time, which results in pharmacokinetic Interactions that can lead to alterations in responsiveness to one or both drugs. In summary, physiological (e.g., age), pathological (e.g., disease effects), and pharmacological (e.g., drug interaction) factors can alter the disposition of drugs in animals. Increased variability among individuals ensuing therefrom may result in therapeutic failure or toxicity in drugs with a narrow therapeutic index.

The patient population that would benefit from a treatment regimen of the present invention is quite diverse, e.g., patients with impaired kidney function are good candidates because continuous levels of protein therapeutics are often associated with renal glomerular deposits. The utility of a therapeutic regimen that does not maintain constant plasma levels as is described in this invention would, therefore, be very beneficial for patients with compromised renal function in which any diminution of existing function could be deleterious. Similarly, brief and intermittent exposure to a therapeutic such as GGF2, as described herein, can be beneficial for patients with tumor types that are responsive to chronic and continuous stimulation with a growth factor. Other patients that may specifically benefit from intermittent therapy as described herein are patients with schwannomas and other peripheral neuropathies. It is an advantage of the present invention that intermittent dosing may have significant advantages in not maintaining continuous side-effect-related stimulation of various tissues.

The proper timing of blood sampling for the purposes of determining serum drug level, as well as the interpretation of the reported level require consideration of the pharmacokinetic properties of the drug being measured. Some terms used in discussion of these properties are defined in the following paragraphs.

Half-Life: The time required for the serum concentration present at the beginning of an interval to decrease by 50%. Knowing an approximate half-life is essential to the clinician since it determines the optimal dosing schedule with oral agents, the intradose fluctuation of the serum concentration, and the time required to achieve steady state.

In brief, multiple pharmacokinetic studies have been performed for GGF2. Typical half-lives for GGF2 are between 4 and 8 hours for the intravenous (iv) route, whereas the half-life of subcutaneously (sc) administered GGF2 is between 11 and 15 hours. Cmax, AUC, Tmax and T1/2 are shown in Tables 1 and 2 below. Where the half-life was too long to be determined accurately by these methods a dash is presented in lieu of a time.

Table 1 and Table 2

APPENDIX 7

Mean Pharmacokinetics of 125I-rhGGF2-Derived Radioactivity in Plasma of Male Sprague-Dawley Rats Following a Single Intravenous or Subcutaneous Dose of 125I-rhGGF2

| Parameters | Group 1 (n = 2) | | Group 2 (n = 1) | |
| --- | --- | --- | --- | --- |
| | Total | TCA Precip | Total | TCA Precip |
| Cmax (ug eq/g) | 0.3289 | 0.2953 | 0.0157 | 0.01 |
| AUC 0-t (ug eq-h/g) | 1.27 | 0.01 | 0.27 | 0.17 |
| AUC inf (ug eq-h/g) | 1.37 | 0.96 | 0.39 | 0.26 |

APPENDIX 7-continued

Mean Pharmacokinetics of 125I-rhGGF2-Derived Radioactivity in Plasma of Male Sprague-Dawley Rats Following a Single Intravenous or Subcutaneous Dose of 125I-rhGGF2

| Parameters | Group 1 (n = 2) | | Group 2 (n = 1) | |
| --- | --- | --- | --- | --- |
| | Total | TCA Precip | Total | TCA Precip |
| Tmax (h) | 0.08 | 0.08 | 6.0 | 6.0 |
| Half-life | 6.37 | 6.11 | 13.20 | 14.66 |

Group 1—i.v.
Group 2—s.c.

APPENDIX 9

Mean Pharmacokinetics of 125I-rhGGF2-Derived Radioactivity in Plasma of Male Sprague-Dawley Rats Following a Single Intravenous or Subcutaneous Dose of 125I-rhGGF2

| Parameters | Group 1 (n = 2) | | Group 2 (n = 1) | |
| --- | --- | --- | --- | --- |
| | Total | TCA Precip | Total | TCA Precip |
| Cmax (ug eq/g) | 0.2611 | 0.2291 | 0.0197 | 0.0034 |
| AUC 0-t (ug eq-h/g) | 1.488 | 0.567 | 0.335 | 0.064 |
| AUC inf (ug eq-h/g) | 1.667 | 0.62 | — | — |
| Tmax (h) | 0.08 | 0.08 | 12.0 | 12.0 |
| Half-life | 7.75 | 7.96 | — | — |

Group 1—i.v.
Group 2—s.c.

Figure 6:
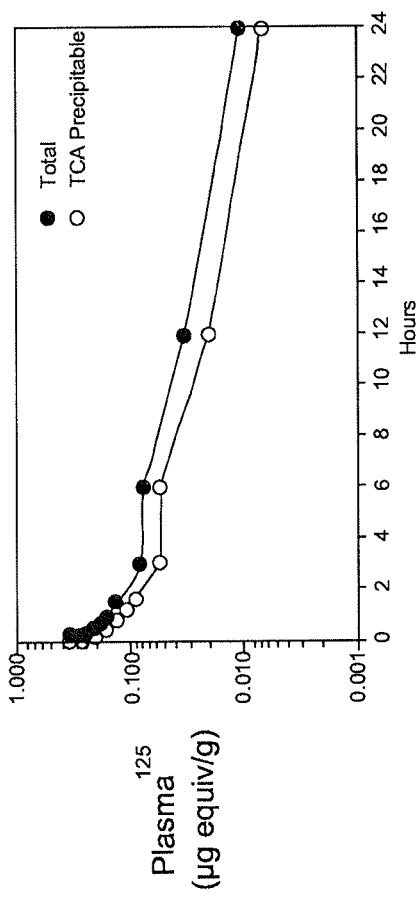
FIG. 6 shows a line graph depicting the half-life of recombinant human GGF2 (rhGGF2) following iv administration.
Figure 7:
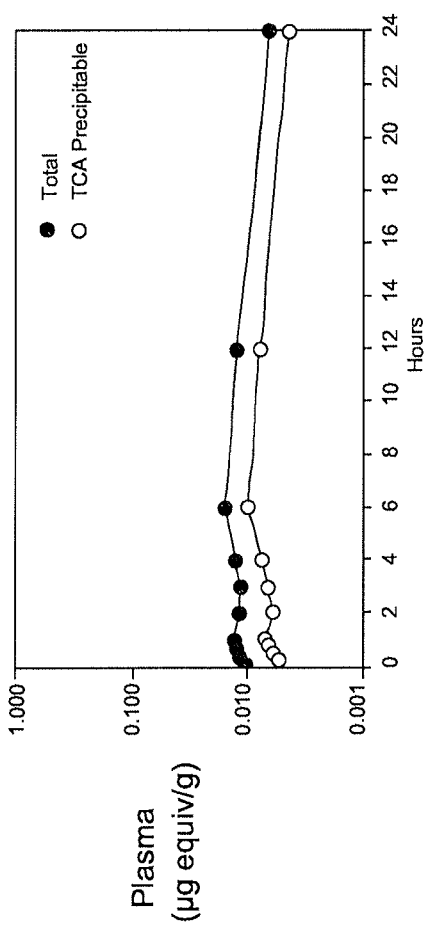
FIG. 7 shows a line graph depicting the half-life of recombinant human GGF2 (rhGGF2) following subcutaneous administration.

The plasma concentrations after administration are shown in FIGS. 6 and 7 for iv and sc administration, respectively. As shown in FIGS. 6 and 7, Cmax, refers to maximal plasma concentration (the maximum concentration that is measured in the plasma at any time after administration); AUCinf, refers to the area under the concentration versus time curve to time infinity (which method is used to anticipate that the assay has limits of detection); AUC0-t, refers to the area under the plasma concentration (time curve from time zero to the last measurable concentration); AUC by any method refers to an estimate of the total exposure to the animal; and Tmax, refers to the median time of maximal plasma concentration.

As is evident from the tables and figures it is not possible to maintain steady state therapeutic levels by either dosing route with every fourth day, every other day or every day of dosing. Levels are unmeasurable after a day and even long before that, as reflected by the data set forth in Table 11.

TABLE 11

PK Parameters for GGF2 after Intravenous Administration*

| Dose (mg/kg) | $AUC_{0-\infty}$ (hr · ng/mL) | $AUC_{0-\infty}$/Dose ((hr · ng/mL)/mg/kg) | $AUC_{0-last}$ (hr · ng/mL) | $AUC_{0-last}$/Dose ((hr · ng/mL)/mg/kg) | CL (mL/min/kg) | $t_{1/2}$ (h) | $V_{SS}$ (mL/kg) |
| --- | --- | --- | --- | --- | --- | --- | --- |
| | | | Rats | | | | |
| 8 | 16100 ± 20500 | 2010 ± 2560 | 16800 ± 22300 | 2100 ± 2790 | 18.1 ± 12.7 | 1.46 ± 1.84 | 1050 ± 331 |
| 16 | 39600 ± 9440 | 2470 ± 590 | 38300 ± 10000 | 2390 ± 625 | 7.00 ± 1.33 | 1.69 ± 0.430 | 532 ± 145 |
| | | | Monkeys | | | | |
| 8 | 15900 ± 1690 | 1980 ± 212 | 15100 ± 1730 | 1890 ± 217 | 8.48 ± 0.910 | 2.02 ± 0.358 | 1110 ± 113 |

*taken from data obtained from plasma GGF2 concentrations measured by ELISA. Data reported are mean ± SD.

Steady State: Steady state serum concentrations are those values that recur with each dose and represent a state of equilibrium between the amount of drug administered and the amount being eliminated in a given time interval. During long term dosage with any drug, the two major determinants of its mean steady state serum concentration are the rate at which the drug is administered and the drug's total clearance in that particular patient.

Peak Serum Concentration: The point of maximum concentration on the serum concentration-versus-time curve. The exact time of the peak serum concentration is difficult to predict since it represents complex relationships between input and output rates.

Trough Serum Concentration: The minimum serum concentration found during a dosing interval. Trough concentrations are theoretically present in the period immediately preceding administration of the next dose.

Absorption: The process by which a drug enters the body. Intravascularly administered drugs are absorbed totally, but extravascular administration yields varying degrees and rates of absorption. The relationship between the rate of absorption and the rate of elimination is the principle determinant of the drug concentration in the bloodstream.

Distribution: The dispersion of the systemically available drug from the intravascular space into extravascular fluids and tissues and thus to the target receptor sites.

Therapeutic Range: That range of serum drug concentrations associated with a high degree of efficacy and a low risk of dose-related toxicity. The therapeutic range is a statistical concept: it is the concentration range associated with therapeutic response in the majority of patients. As a consequence, some patients exhibit a therapeutic response at serum levels below the lower limit of the range, while others require serum levels exceeding the upper limit for therapeutic benefit.

Correct timing of sample collection is important, since drug therapy is often revised on the basis of serum concentration determinations. The absorption and distribution phases should be complete and a steady-state concentration achieved before the sample is drawn. Levels obtained before a steady-state concentration exists may be erroneously low; increasing the dosage based on such a result could produce toxic concentrations. In addition, when making comparative measurements, it is important that the sampling time be consistent.

The timing of blood samples in relation to dosage is critical for correct interpretation of the serum concentration result. The selection of the time that the sample is drawn in relation to drug administration should be based on the pharmacokinetic properties of the drug, its dosage form and the clinical reason for assaying the sample (e.g., assessment of efficacy or clarification of possible drug-induced toxicity). For routine serum level monitoring of drugs with short half-lives, both a steady state peak and trough sample may be collected to characterize the serum concentration profile; for drugs with a long half-life, steady-state trough samples alone are generally sufficient.

By "congestive heart failure" is meant impaired cardiac function that renders the heart unable to maintain the normal blood output at rest or with exercise, or to maintain a normal cardiac output in the setting of normal cardiac filling pressure. A left ventricular ejection fraction of about 40% or less is indicative of congestive heart failure (by way of comparison, an ejection fraction of about 60% percent is normal). Patients in congestive heart failure display well-known clinical symptoms and signs, such as tachypnea, pleural effusions, fatigue at rest or with exercise, contractile dysfunction, and edema. Congestive heart failure is readily diagnosed by well known methods (see, e.g., "Consensus recommendations for the management of chronic heart failure." Am. J. Cardiol., 83(2A): 1A-38-A, 1999).

Relative severity and disease progression are assessed using well known methods, such as physical examination, echocardiography, radionuclide imaging, invasive hemodynamic monitoring, magnetic resonance angiography, and exercise treadmill testing coupled with oxygen uptake studies.

By "ischemic heart disease" is meant any disorder resulting from an imbalance between the myocardial need for oxygen and the adequacy of the oxygen supply. Most cases of ischemic heart disease result from narrowing of the coronary arteries, as occurs in atherosclerosis or other vascular disorders.

By "myocardial infarction" is meant a process by which ischemic disease results in a region of the myocardium being replaced by scar tissue.

By "cardiotoxic" is meant a compound that decreases heart function by directly or indirectly impairing or killing cardiomyocytes.

By "hypertension" is meant blood pressure that is considered by a medical professional (e.g., a physician or a nurse) to be higher than normal and to carry an increased risk for developing congestive heart failure.

By "treating" is meant that administration of a neuregulin or neuregulin-like peptide slows or inhibits the progression of congestive heart failure during the treatment, relative to the disease progression that would occur in the absence of treatment, in a statistically significant manner. Well known indicia such as left ventricular ejection fraction, exercise performance, and other clinical tests as enumerated above, as well as survival rates and hospitalization rates may be used to assess disease progression. Whether or not a treatment slows or inhibits disease progression in a statistically significant manner may be determined by methods that are well known in the art (see, e.g., SOLVD Investigators, N. Engl. J. Med. 327:685-691, 1992 and Cohn et al., N. Engl. J Med. 339:1810-1816, 1998).

By "preventing" is meant minimizing or partially or completely inhibiting the development of congestive heart failure in a mammal at risk for developing congestive heart failure (as defined in "Consensus recommendations for the management of chronic heart failure." Am. J. Cardiol., 83(2A): 1A-38-A, 1999). Determination of whether congestive heart failure is minimized or prevented by administration of a neuregulin or neuregulin-like peptide is made by known methods, such as those described in SOLVD Investigators, supra, and Cohn et al., supra.

The term "therapeutically effective amount" is intended to mean that amount of a drug or pharmaceutical agent that elicits the biological or medical response of a tissue, a system, animal or human that is being sought by a researcher, veterinarian, medical doctor or other clinician. A therapeutic change is a change in a measured biochemical characteristic in a direction expected to alleviate the disease or condition being addressed. More particularly, a "therapeutically effective amount" is an amount sufficient to decrease the symptoms associated with a medical condition or infirmity, to normalize body functions in disease or disorders that result in impairment of specific bodily functions, or to provide improvement in one or more of the clinically measured parameters of a disease.

The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician.

The term "therapeutic window" is intended to mean the range of dose between the minimal amount to achieve any therapeutic change, and the maximum amount which results in a response that is the response immediately before toxicity to the patient.

By "at risk for congestive heart failure" is meant an individual who smokes, is obese (i.e., 20% or more over their ideal weight), has been or will be exposed to a cardiotoxic compound (such as an anthracycline antibiotic), or has (or had) high blood pressure, ischemic heart disease, a myocardial infarct, a genetic defect known to increase the risk of heart failure, a family history of heart failure, myocardial hypertrophy, hypertrophic cardiomyopathy, left ventricular systolic dysfunction, coronary bypass surgery, vascular disease, atherosclerosis, alcoholism, periocarditis, a viral infection, gingivitis, or an eating disorder (e.g., anorexia nervosa or bulimia), or is an alcoholic or cocaine addict.

By "decreasing progression of myocardial thinning" is meant maintaining hypertrophy of ventricular cardiomyocytes such that the thickness of the ventricular wall is maintained or increased.

By "inhibits myocardial apoptosis" is meant that neuregulin treatment inhibits death of cardiomyocytes by at least 10%, more preferably by at least 15%, still more preferably by at least 25%, even more preferably by at least 50%, yet more preferably by at least 75%, and most preferably by at least 90%, compared to untreated cardiomyocytes.

By "neuregulin" or "NRG" is meant a peptide that is encoded by an NRG-1, NRG-2, or NRG-3 gene or nucleic acid (e.g., a cDNA), and binds to and activates ErbB2, ErbB3, or ErbB4 receptors, or combinations thereof.

By "neuregulin-1," "NRG-1," "heregulin," "GGF2," or "p185erbB2 ligand" is meant a peptide that binds to the ErbB2 receptor when paired with another receptor (ErbB1, ErbB3 or ErbB4) and is encoded by the p185erbB2 ligand gene described in U.S. Pat. Nos. 5,530,109; 5,716,930; and 7,037,888, each of which is incorporated herein by reference in its entirety.

By "neuregulin-like peptide" is meant a peptide that possesses an EGF-like domain encoded by a neuregulin gene, and binds to and activates ErbB2, ErbB3, ErbB4, or a combination thereof.

By "epidermal growth factor-like domain" or "EGF-like domain" is meant a peptide motif encoded by the NRG-1, NRG-2, or NRG-3 gene that binds to and activates ErbB2, ErbB3, ErbB4, or combinations thereof, and bears a structural similarity to the EGF receptor-binding domain as disclosed in Holmes et al., Science 256:1205-1210, 1992; U.S. Pat. No. 5,530,109; 5,716,930; 7,037,888; Hijazi et al., Int. J. Oncol. 13:1061-1067, 1998; Chang et al., Nature 387:509-512, 1997; Carraway et al., Nature 387:512-516, 1997; Higashiyama et al., J Biochem. 122:675-680, 1997; and WO 97/09425). See FIGS. 9-14 for nucleic and amino acid sequences corresponding to EGFL domains 1-6 encoded by the NRG-1 gene.

By "anti-ErbB2 antibody" or "anti-HER2 antibody" is meant an antibody that specifically binds to the extracellular domain of the ErbB2 (also known as HER2 in humans) receptor and prevents the ErbB2 (HER2)-dependent signal transduction initiated by neuregulin binding.

By "transformed cell" is meant a cell (or a descendent of a cell) into which a DNA molecule encoding a neuregulin or peptide having a neuregulin EGF-like domain has been introduced, by means of recombinant DNA techniques or known gene therapy techniques.

By "promoter" is meant a minimal sequence sufficient to direct transcription. Also included in the invention are those promoter elements which are sufficient to render promoter-dependent gene expression controllable based on cell type or physiological status (e.g., hypoxic versus normoxic conditions), or inducible by external signals or agents; such elements may be located in the 5' or 3' or internal regions of the native gene.

By "operably linked" is meant that a nucleic acid encoding a peptide (e.g., a cDNA) and one or more regulatory sequences are connected in such a way as to permit gene expression when the appropriate molecules (e.g., transcriptional activator proteins) are bound to the regulatory sequences.

By "expression vector" is meant a genetically engineered plasmid or virus, derived from, for example, a bacteriophage, adenovirus, retrovirus, poxvirus, herpesvirus, or artificial chromosome, that is used to transfer a peptide (e.g., a neuregulin) coding sequence, operably linked to a promoter, into a host cell, such that the encoded peptide or peptide is expressed within the host cell.

Unless defined otherwise, all technical and scientific terms used herein have the same meaning as commonly understood by one of ordinary skill in the art to which this invention belongs.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention before the priority date of each claim of this application.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure within known or customary practice within the art to which the invention pertains and may be applied to the essential features hereinbefore set forth, and follows in the scope of the appended claims.

The following Examples will assist those skilled in the art to better understand the invention and its principles and advantages. It is intended that these Examples be Illustrative of the Invention and not limit the scope thereof.

EXAMPLES

As indicated herein above, the neuregulins are a family of growth factors structurally related to Epidermal Growth Factor (EGF) and are essential for the normal development of the heart. Evidence suggests that neuregulins are a potential therapeutic for the treatment of heart disease including heart failure, myocardial infarction, chemotherapeutic toxicity and viral myocarditis.

The studies described herein were served to define dosing in the left anterior descending (LAD) artery ligation model of congestive heart failure in the rat. Multiple neuregulin splice variants were cloned and produced. A neuregulin fragment of consisting of the EGF-like domain (EGF-1d) from previous reports (Liu et al., 2006) was compared to a full-length neuregulin known as glial growth factor 2

(GGF2) and the EGF-like domain with the Ig domain (EGF-Ig). Male and female Sprague-Dawley rats underwent LAD artery ligation. At 7 days post ligation rats were treated intravenously (iv) with neuregulin daily. Cardiac function was monitored by echocardiography.

The first study compared 10 days of dosing with equimolar amounts of EGF-1d or GGF2 (for GGF2 this calculates to 0.0625 and 0.325 mg/kg). GGF2 treatment resulted in significantly ($p<0.05$) greater improvement in Ejection Fraction (EF) and Fractional Shortening (FS) than did EGF-1d at the end of the dosing period. The second study compared 20 days of GGF2 with EGF-1d and EGF-Ig at equimolar concentrations. GGF2 treatment resulted in significantly improved EF, FS and LVESD ($p<0.01$). Improvements in cardiac physiology were not maintained for this period with either EGF-1d or EGF-Ig. The third study compared daily (q 24 hour), every other day (q 48 hour) and every fourth day (q 96 hour) dosing for 20 days with GGF2 (3.25 mg/kg). All three GGF2 treatment regimens resulted in significant improvements in cardiac physiology including EF, ESV and EDV and the effects were maintained for 10 days following termination of dosing. The studies presented here confirm GGF2 as the lead neuregulin compound and establish optimal dosing regimens for administering same.

As shown herein, the present studies establish the relative efficacy of GGF2 compared with published neuregulin fragments (Liu et al., 2006), initiate dose ranging and dose frequency studies, and determine if BSA excipient is required as previously reported.

Methods and Materials

Cloning, expression and purification of the IgEGF (Ig154Y) domain of GGF2 (EGF-Ig) DNA: IgEGF domain was amplified from an existing GGF2 cDNA and cloned into pet 15b vector (Novagen cat #69661-3) using Nde1 and BamH1 restriction sites. The resulting protein is a 21.89 kda+~3 kDa His tag (=~25 kDa)

DNA sequence of IgEgf pet 15 clone: The underlined sequences are the primers used for amplification. The bolded sequences are the cloning sites used to insert the sequence into the pet vector (Nde1 and BamH1).

```
CATATGttgcctccccaattgaaagagatgaaaagccaggaatcggctgcaggttccaaa
     L  P  P  Q  L  K  E  M  K  S  Q  E  S  A  A  G  S  K ctagtccttcggtgtgaaaccagttctgaatactcctctctcagattcaagtggttcaag
 L  V  L  R  C  E  T  S  S  E  Y  S  S  L  R  F  K  W  F  K aatgggaatgaattgaatcgaaaaaacaaaccacaaaatatcaagatacaaaaaaagcca
 N  G  N  E  L  N  R  K  N  K  P  Q  N  I  K  I  Q  K  K  P gggaagtcagaacttcgcattaacaaagcatcactggctgattctggagagtatatgtgc
 G  K  S  E  L  R  I  N  K  A  S  L  A  D  S  G  E  Y  M  C aaagtgatcagcaaattaggaaatgacagtgcctctgccaatatcaccatcgtggaatca
 K  V  I  S  K  L  G  N  D  S  A  S  A  N  I  T  I  V  E  S aacgctacatctacatccaccactgggacaagccatcttgtaaaatgtgcggagaaggag
 N  A  T  S  T  S  T  T  G  T  S  H  L  V  K  C  A  E  K  E aaaactttctgtgtgaatggaggggagtgcttcatggtgaaagacctttcaaacccctcg
 K  T  F  C  V  N  G  G  E  C  F  M  V  K  D  L  S  N  P  S agatacttgtgcaagtgcccaaatgagtttactggtgatcgctgccaaaactacgtaatg
 R  Y  L  C  K  C  P  N  E  F  T  G  D  R  C  Q  N  Y  V  N
```

(SEQ ID NO: 15)

```
gccagcttctacGGATCC
 A  S  F  Y
```

(SEQ ID NO: 16)

The final translated protein from pet15b vector is shown below. The vector portion is underlined.

(SEQ ID NO: 17)

M G G S H H H H H H G M A S M T G G T A N G

V G D L Y D D D D K V P G S L P P Q L K E M

K S Q E S A A G S K L V L R C E T S S E Y S

S L R F K W F K N G N E L N R K N K P Q N I

K I Q K K P G K

-continued

```
S E L R I N K A S L A D S G E Y M C K V I S

K L E N D S A S A N I T I V E S N A T S T S

T T G T S H L V K C A E K E K T F C V N G G

E C F M V K D L S N P S R Y L C K C P N E F

T G D R C Q N Y V M A S F Y
```

Protein expression: The clone was transformed into 8121 cells for protein expression using the Overnight Express Autoinduction System (Novagen) in LB media at 25° C. for 24 hours.

Protein Refolding: Adapted from Novagen Protein Refolding Kit, 70123-3.

Protein Purification: His TRAP columns—as per manufacturer's instructions

Western blotting: Protein expression was assessed by western blotting. Resulting band with the His tag runs at around 25 kD.

A 4-20% criterion gel (Biorad) was used for protein resolution followed by transfer onto Protran nitrocellulose paper (0.1 µm pore size from Schliecher and Schull). The blot is blocked in 5% milk in TBS-T (0.1%). Primary antibody (Anti EGF Human NRG I-alpha/HRG I-alpha Affinity Purified Polyclonal Ab Cat #AF-296-NA from R&D systems) 1:1000 dilution in 5% milk in TBS-T-1 hour at RT (also works at 4° C. overnight). Rabbit anti goat HRP secondary antibody was used at 1:10,000 dilution in 5% milk in TBS-T for 1 hour at RT. All washes were performed in TBS-T Purification Protocol for Ig154Y: The cultures are grown at 25° C. in Overnight Express Autoinduction System 1 from Novagen (cat#71300-4). The culture is spun down and the pellets are extracted, solubilized and re-folded to acquire the Ig154Y before purification can take place.

Materials for Extraction, Solubilization and Re-Folding:
10× Wash Buffer: 200 mM Tris-HCl, pH 7.5, 100 mM EDTA, 10% Triton X-100
10× Solubilization Buffer: 500 mM CAPS, pH 11.0
50× Dialysis Buffer: 1M Tris-HCl, pH 8.5
30% N-laurylsarcosine—add as powder (Sigma 61739-5G)
1M DTT
Reduced glutathione (Novagen 3541)
Oxidized glutathione (Novagen 3542)

A. Cell Lysis and Preparation of Inclusion Bodies
  Cell pellets were thawed and re-suspended in 30 mls 1× wash buffer.
  Protease inhibitors (25 ul of 10× per 50 mls), DNase (200 ul of 1 mg/ml per 50 ml) and $MgCl_2$ (500 ul of 1M per 50 mls) were added to suspension.
  Cells were lysed by sonication with cooling on Ice.
  Following sonication inclusion bodies were collected by centrifugation at 10000×g for 12 minutes.
  Supernatant was removed and the pellet thoroughly re-suspended in 30 mls of 1× Wash Buffer.
  Step 4 was repeated.
  The pellet was thoroughly re-suspended in 30 mls of 1× Wash Buffer.
  The inclusion bodies were collected by centrifugation at 10000×g for 10 minutes.

B. Solubilization and Refolding
  From the wet weight of inclusion bodies to be processed, calculate the amount of 1× Solubilization Buffer necessary to re-suspend the inclusion bodies at a concentration of 10-15 mg/ml. If the calculated volume is greater than 250 ml, use 250 ml.
  At room temperature, prepare the calculated volume of 1× Solubilization Buffer supplemented with 0.3% N-laurylsarcosine (up to 2% may be used if needed in further optimization) (300 mg/100 mL buffer) and 1 mM DTT.
  Add the calculated amount of 1× Solubilization Buffer from step 2 to the inclusion bodies and gently mix. Large debris can be broken up by repeated pipetting.
  Incubate in refrigerator shaker at 25° C., 50-100 rpm for 4-5 hours (or longer if needed in further optimization).
  Clarify by centrifugation at 10000×g for 10 minutes at room temperature
  Transfer the supernatant containing the soluble protein into a clean tube.

C. Dialysis Protocol for Protein Refolding
  Prepare the required volume of buffer for dialysis of solubilized protein. The dialysis should be performed with at least 2 buffer changes of greater than 50 times the volume of the sample. Dilute the 50× Dialysis Buffer to 1× at the desired volume and supplement with 0.1 mM DTT.
  Dialyze for at least 4 hours at 4° C. Change the buffer and continue. Dialyze for an additional 4 or more hours.
  Prepare additional dialysis buffer as determined in step 1, but omit DTT.
  Continue the dialysis through two additional changes (minutes 4 hr each), with the dialysis buffer lacking DTT.

D. Redox Refolding Buffer to Promote Disulfide Bond Formation
  Prepare a dialysis buffer containing 1 mM reduced glutathione (1.2 g/4 L) and 0.2 mM oxidized glutathione (0.48 g/4 L) in 1× Dialysis Buffer. The volume should be 25 times greater than the volume of the solubilized protein sample. Chill to 4° C.
  Dialyze the refolded protein from step 1 overnight at 4° C.

Materials for Purification
All procedures are done at 4° C.
Chemicals:
Trizma Hydrochloride (Sigma T5941-500G)
Sodium Chloride 5M Solution (Sigma S6546-4L)
Sodium Hydroxide 10N (JT Baker 5674-02)
Imidazole (JT Baker N811-06)

A. Purification on the HISPrep FF 16/10 Column—20 mls (GE Healthcare)
Buffer A: 20 mM Tris-HCL+500 mM NaCl pH 7.5
Buffer B: Buffer A+500 mM Imidazole pH 7.5
Equilibration of column: Buffer A—5CV, Buffer B—5CV, Buffer A—10CV
Load 20 ml of sample per run on 20 ml column at 0.5 ml/min
Wash column with 5CV of buffer A
Elute column with 5CV of 280 mM Imidazole.
Clean with 10CV of 100% Buffer B.
Equilibrate with 15CV of Buffer A
Analyze fractions with a SDS-page silver stain
Pool fractions with Ig154Y B. His-Tag Removal Removal of the His-Tag is done with A Thrombin Cleavage Capture Kit from Novagen (Cat#69022-3). Based on previous testing, the best conditions are room temperature for 4 hours with Thrombin at 0.005 U of enzyme per μl for every 10 μg of Ig154Y protein. After four hours of incubation, add 16 μl of Streptavidin Agarose slurry per unit of Thrombin enzyme. Rock sample for 30 minutes at room temp. Recover the Ig154Y through spin-filtration or sterile filtering (depending on volume).

Full cleavage is determined by EGF and Anti-His western blotting.

C. Concentration of Ig154Y

Adjust to desired concentration with Millipore Centriprep 3000 MWCO 15 ml concentrator (Ultracel YM-3, 4320)

D. Storage in Final Buffer

Store in 20 mM Tris+500 mM NaCl pH 7.5 and 1×PBS+ 0.2% BSA.

Cloning, Expression and Purification of 156Q (EGF-1d) [NRG1b2 EGF Domain (156Q)]DNA: NRG1b2 egf domain was cloned from human brain cDNA and cloned into pet 15b vector (Novagen cat #69661-3) using Nde1 and BamH1 restriction sites. The resulting protein is a 6.92 kda+~3 kDa His tag (=9.35 kDa)

DNA sequence of NRG1 b2 egf pet 15 clone

The underlined sequences are the cloning sites (Nde1 and BamH1)

```
                                              (SEQ ID NO: 18)
CATATGAGCCA TCTTGTAAAA TGTGcGGAGA AGGAGAAAAC

TTTCTGTGTG AATGGAGGGG AGTGCTTCAT GGTGAAAGAC

CTTTCAAACC CCTCGAGATA CTTGTGCAAC TGCCCAAATG

AGTTTACTGG TGATCGCTGC CAAAACTACG TAATGGCCAG

CTTCTACAAG GCGGAGGAGC TGTACCAGTA AGGATCC
```

The final translated protein from pet15b vector is shown below. The egf domain is highlighted in green.

```
                10                  20
MGSSHHHHHH SSGLVPRGSH MSHLVKCAEK EKTFCVNGGE

30
CFMVKDLSNP 60              70              80
SRYLCKCPNE FTGDRCQNYV MASFYKAEEL YQ (SEQ ID NO: 19)
```

Calculated pI/Mw: 7.69/9349.58

Protein Expression

The clone was transformed into Bl21 cells for protein expression using the Overnight Express Autoinduction System (Novagen) in LB media at 25° C. for 24 hours. Expression is primarily in insoluble inclusion bodies.

Protein Refolding: Adapted from Novagen Protein Refolding Kit, 70123-3.

Protein Purification: Protein is loaded onto an anion exchange column DEAE at 2.5 ml/min. The EGF-1d fragment remains in the flow through, whereas the contaminants bind and elute at a higher salt. The loading and washing buffer is 50 mM Tris pH7.9 and elution buffer is 50 mM Tris pH7.9 with 1 M NaCl. The flow through is pooled and concentrated with Centriprep YM-3 from Millipore.

Western Blotting: Protein expression is assessed by western blotting. Resulting band runs at around 10 kD.

A 4-20% criterion gel (Biorad) was used for protein resolution followed by transfer onto Protran nitrocellulose paper (0.1 μm pore size from Schliecher and Schull). The blot is blocked in 5% milk in TBS-T (0.1%). Primary antibody (Anti EGF Human NRG1-alpha/HRG1-alpha Affinity Purified Polyclonal Ab Cat #AF-296-NA from R&D systems) 1:1000 dilution in 5% milk in TBS-T-1 hour at RT (also works at 4° C. overnight). Rabbit anti goat HRP secondary antibody was used at 1:10,000 dilution in 5% milk in TBS-T for 1 hour at RT. All washes were performed in TBS-T Purification Protocol for NRG-1560

The cultures are grown at 25° C. in Overnight Express Autoinduction System 1 from Novagen (cat#71300-4). There is very little soluble NRG-156Q (EGF-1d) present. The culture is spun down and the pellets are extracted, solubilized and re-folded to acquire the NRG-156Q before purification can take place.

Materials for Extraction, Solubilization and Re-Folding:

10× Wash Buffer: 200 mM Tris-HCl, pH 7.5, 100 mM EDTA, 10% Triton X-100

10× Solubilization Buffer: 500 mM CAPS, pH 11.0

50× Dialysis Buffer: 1M Tris-HCl, pH 8.5

30% N-laurylsarcosine—add as powder (Sigma 61739-5G)

1M DTT

Reduced glutathione (Novagen 3541)

Oxidized glutathione (Novagen 3542)

A. Cell Lysis and Preparation of Inclusion Bodies

Thaw and re-suspend cell pellet in 30 mls 1× wash buffer. Mix as needed for full re-suspension.

Add protease inhibitors (25 ul of 10× per 50 mls), DNase (200 ul of 1 mg/ml per 50 ml) and MgCl2 (500 ul of 1 M per 50 mls) to suspension.

Lyse the cells by sonication.
  a. Cool the cells on ice throughout this step.
  b. Using the square tip, sonicate for 30 seconds on level 6, 10 times until suspension becomes less viscous. Let suspension cool on ice for 60 seconds between each sonication. Keep volume no higher than 40 mls in 50 ml conical tube when sonicating.

When complete, transfer each suspension to 250 ml angled neck centrifuge bottles for use with F-16/250 rotor.

Collect the inclusion bodies by centrifugation at 10,000×g for 12 minutes.

Remove the supernatant (save a sample for analysis of soluble protein) and thoroughly re-suspend the pellet in 30 mls of 1× Wash Buffer.

Repeat centrifugation as in Step 4 and save the pellet.

Again, thoroughly re-suspend the pellet in 30 mls of 1× Wash Buffer.

Collect the inclusion bodies by centrifugation at 10,000×g for 10 minutes. Decant the supernatant and remove the last traces of liquid by tapping the inverted tube on a paper towel.

B. Solubilization and Refolding

From the wet weight of inclusion bodies to be processed, calculate the amount of 1× Solubilization Buffer necessary to re-suspend the inclusion bodies at a concentration of 10-15 mg/ml. If the calculated volume is greater than 250 ml, use 250 ml.

At room temperature, prepare the calculated volume of 1× Solubilization Buffer supplemented with 0.3% N-laurylsarcosine (up to 2% may be used if needed in further optimization) (300 mg/100 mL buffer) and 1 mM DTT.

Add the calculated amount of 1× Solubilization Buffer from step 2 to the inclusion bodies and gently mix. Large debris can be broken up by repeated pipetting.

Incubate in refrigerator shaker at 25° C., 50-100 rpm for 4-5 hours.

Clarify by centrifugation at 10,000×g for 10 minutes at room temperature.

C. Dialysis Protocol for Protein Refolding

Prepare the required volume of buffer for dialysis of solubilized protein. The dialysis should be performed with at least 2 buffer changes of greater than 50 times the volume of the sample.

Dilute the 50× Dialysis Buffer to 1× at the desired volume and supplement with 0.1 mM DTT.

Dialyze for at least 4 hours at 4° C. Change the buffer and continue. Dialyze for an additional 4 or more hours.

Prepare additional dialysis buffer as determined in step 1, but omit DTT.

Continue the dialysis through two additional changes (minutes 4 hours each), with the dialysis buffer lacking DTT.

D. Redox Refolding Buffer to Promote Disulfide Bond Formation

Prepare a dialysis buffer containing 1 mM reduced glutathione (1.2 g/4 L) and 0.2 mM oxidized glutathione (0.48 g/4 L) in 1× Dialysis Buffer. The volume should be 25 times greater than the volume of the solubilized protein sample. Chill to 4° C.

Dialyze the refolded protein from step 1 overnight at 4° C.

Materials for Purification

All procedures are done at 4° C.

Chemicals:

Trizma Hydrochloride (Sigma T5941-500G)

Sodium Chloride 5M Solution (Sigma S6546-4L)

Sodium Hydroxide 10N (JT Baker 5674-02)

E. Purification on the DEAE HiPrep 16/10 Anion Column—20 mls (GE Healthcare)

Buffer A: 50 mM Tris-HCL pH 8.0

Buffer B: 50 mM Tris-HCL with 1 M NaCl pH 8.0

Equilibration of column: Buffer A—5CV, Buffer B—5CV, Buffer A—10CV

Load 50 ml of sample per run on 20 ml column at 2.0 ml/min (NRG-156 (EGF-Id) is in the flow through).

Wash 20 ml column with 5CV of buffer A 20 ml column with gradient to 100% B with 5CV. This is to elute off contaminants.

Clean with 10CV of 100% Buffer B.

Equilibrate with 15CV of Buffer A

Analyze fractions with a SDS-page silver stain

Pool fractions with NRG-156Q (10 kDa)

F. Concentration of NRG-156 (EGF-Id)

Concentrate with Millipore Centriprep 3000 MWCO 15 ml concentrator (Ultracel YM-3, 4320)

Use Modified Lowry Protein Assay to determine concentration.

G. His-Tag Removal

Removal of the His-Tag is done with A Thrombin Cleavage Capture Kit from Novagen (Cat#69022-3). Based on previous testing the best conditions are room temperature for 4 hours with Thrombin at 0.005 U of enzyme per µl for every 10 g of NRG-156Q (EGF-Id) protein. After four hours of incubation, add 16 µl of Streptavidin Agarose slurry per unit of Thrombin enzyme. Rock sample for 30 minutes at room temperature. Recover the NRG-156Q through spin-filtration or sterile filtering (depending on volume). Complete cleavage is determined with an EGF and Anti-His western.

H. Storage in Final Buffer

Stored in 1×PBS with 0.2% BSA at 4° C.

Expression and Purification of GGF2

For the cloning and background information for GGF2, see U.S. Pat. No. 5,530,109. The cell line is described in U.S. Pat. No. 6,051,401. The entire contents of each of U.S. Pat. Nos. 5,530,109 and 6,051,401 is incorporated herein by reference in its entirety.

CHO-(Alpha2HSG)-GGF Cell Line: This cell line was designed to produce sufficient quantities of fetuin (human alpha2HSG) to support high production rates of rhGGF2 in serum free conditions.

Cho (dhfr-) cells were transfected with the expression vector shown in FIG. 16 (pSV-AHSG). Stable cells were grown under ampicillin selection. The cell line was designated (dhfr⁻/α2HSGP). The dhfr⁻/α2HSGP cells were then transfected with the pCMGGF2 vector shown in FIG. 16 containing the coding sequence for human GGF2 using the cationic lipid DMRIE-C reagent (Life Technologies #10459-014).

Stable and high producing cell lines were derived under standard protocols using methotrexate (100 nM, 200 nM, 400 nM, 1 µM) at 4-6 weeks intervals. The cells were gradually weaned from serum containing media. Clones were isolated by standard limiting dilution methodologies. Details of the media requirements are found in the above mentioned reports.

Figure 17:
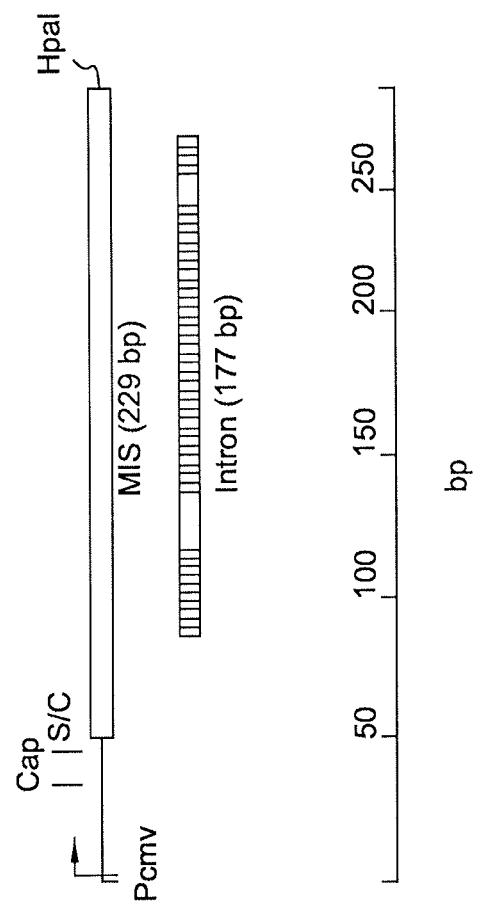
FIG. 17 shows schematic diagrams of GGF2 coding sequence placed after the EBV BMLF-1 intervening sequence (MIS).

To enhance transcription, the GGF2 coding sequence was placed after the EBV BMLF-1 intervening sequence (MIS). See diagrams at FIG. 17.

```
MIS Sequence
                                                      (SEQ ID NO: 20)
CGAT[AACTAGCAGCATTTCCTCCAACGAGGATCCCGCAG(GTAAGAAGCTACACCGGCCAGTGG

CCGGGGCCCGATAACTAGCAGCATTTCCTCCAACGAGGATCCCGCAGGTAAGAAGCTACACCGG

CCAGTGGCCGGGGCCGTGGAGCGGGGCATCCGGTGCCTGAGACAGAGGTGCTCAAGGCAGTCTCC

ACCTTTTGTCTCCCCTCTGCAG)AGAGCCACATTCTGGAA]GTT

GGF2 coding sequence
                                                      (SEQ ID NO: 23)
            atgagatgg cgacgcgccc cgcgccgctc cgggcgtccc 301   ggccccggg cccagcgccc cggctccgcc gcccgctcgt cgccgccgct gccgctgctg 361   ccactactgc tgctgctggg gaccgcggcc ctggcgccgg gggcggcggc cggcaacgag 421   gcggctcccg cggggggcctc ggtgtgctac tcgtccccgc ccagcgtggg atcggtgcag
```

-continued

```
 481  gagctagctc agcgcgccgc ggtggtgatc gagggaaagg tgcacccgca gcggcggcag 541  caggggggcac tcgacaggaa ggcggcggcg gcggcgggcg aggcaggggc gtggggcggc 601  gatcgcgagc cgccagccgc gggcccacgg gcgctggggc cgcccgccga ggagccgctg 661  ctcgccgcca acggaccgt gccctcttgg cccaccgccc cggtgcccag cgccggcgag 721  cccggggagg aggcgcccta tctggtgaag gtgcaccagg tgtgggcggt gaaagccggg 781  ggcttgaaga aggactcgct gctcaccgtg cgcctgggga cctggggcca cccgccttc 841  ccctcctgcg ggaggctcaa ggaggacagc aggtacatct tcttcatgga gcccgacgcc 901  aacagcacca gccgcgcgcc ggccgccttc cgagcctctt tccccctct ggagacgggc 961  cggaaccca agaaggaggt cagccgggtg ctgtgcaagc ggtgcgcctt gcctccccaa 1021  ttgaaagaga tgaaagcca ggaatcggct gcaggttcca aactagtcct tcggtgtgaa 1081  accagttctg aatactcctc tctcagattc aagtggttca agaatgggaa tgaattgaat 1141  cgaaaaaaca aaccacaaaa tatcaagata caaaaaaagc cagggaagtc agaacttcgc 1201  attaacaaag catcactggc tgattctgga gagtatatgt gcaaagtgat cagcaaatta 1261  ggaaatgaca gtgcctctgc caatatcacc atcgtggaat caaacgctac atctacatcc 1321  accactggga caagccatct tgtaaaatgt gcggagaagg agaaaacttt ctgtgtgaat 1381  ggaggggagt gcttcatggt gaaagacctt tcaaacccct cgagatactt gtgcaagtgc 1441  ccaaatgagt ttactggtga tcgctgccaa aactacgtaa tggccagctt ctacagtacg 1501  tccactccct ttctgtctct gcctgaatag
```

GGF2 Protein Sequence
                                                                (SEQ ID NO: 24)
      MRWRRAPRRSGRPGPRAQRPGSAARSSPPLPLLPLLLLLGTAAL
APGAAAGNEAAPAGASVCYSSPPSVGSVQELAQRAAVVIEGKVHPQRRQQGALDRKAA
AAAGEAGAWGGDREPPAAGPRALGPPAEEPLLAANGTVPSWPTAPVPSAGEPGEEAPY
LVKVHQVWAVKAGGLKKDSLLTVRLGTWGHPAFPSCGRLKEDSRYIFFMEPDANSTSR
APAAFRASFPPLETGRNLKKEVSRVLCKRCALPPQLKEMKSQESAAGSKLVLRCETSS
EYSSLRFKWRKNGNELNRKNKPQNIKIQKKPGKSELRINKASLADSGEYMCKVISKLG
NDSASANITIVESNATSTSTTGTSHLVKCAEKEKTFCVNGGECFMVKDLSNPSRYLCK
CPNEFTGDRCQNYVMASFYSTSTPFLSLPE GGF2 production: One vial of GGF2 at 2.2×10⁶ cells/mL was thawed into 100 mls of Acorda Medium 1 (see Table 3) and expanded until reaching sufficient numbers to seed production vessels. Cells were inoculated into the production media Acorda Medium 2 (see Table 4) at 1.0×10⁵ cells/mL in two liter vented roller bottles. Roller bottles are maintained at 37° C. for 5 days and then reduced to 27° C. for 26 days. The roller bottles are monitored for cell count and general appearance but they are not fed. Once viability is below 10% the cells are spun out and conditioned media harvested and sterile filtered.

TABLE 3

| | Medium 1 | | |
|---|---|---|---|
| Item | Vendor | Catalog Number | Final concentration |
| CD-CHO | Invitrogen | 10743-029 | remove 50 ml, then add components below |
| FeSO₄·EDTA | Sigma | F-0518 | 1x (10 ml/L) |
| L-Glutamine | Cellgro | 25-005-CI | 4 mM (20 ml/L) |
| Recombinant Human Insulin | Sigma | I-9278 | 290 U/L (1 ml/L) |
| Non-essential amino acid | Cellgro | 25-025-CI | 1x (10 ml/L) |
| Peptone Type 4 Soybean-HySoy | Sigma | P0521 | Powder - Made 20X in CD-CHO (50 ml/L) |
| Gentamicin | Invitrogen | 15750-078 | 100 µg (2 ml/L) |

TABLE 4

Medium 2

| Item | Vendor | Catalog Number | Final concentration |
|---|---|---|---|
| CD-CHO | Invitrogen | 10743-029 | 50% (~50 ml first) |
| HyQ SFX-CHO | HyClone | SH30187.02 | 50% (~50 ml first) |
| FeSO$_4$•EDTA | Sigma | F-0518 | 1x (10 ml/L) |
| L-Glutamine | Cellgro | 25-005-CI | 4 mM (20 ml/L) |
| Recombinant Human Insulin | Sigma | I-9278 | 290 U/L (1 ml/L) |
| Non-essential amino acid | Cellgro | 25-025-CI | 1x (10 ml/L) |
| Peptone Type 4 Soybean-HySoy | Sigma | P0521 | Powder - Made 20X in CD-CHO (50 ml/L) |
| Gentamicin | Invitrogen | 15750-078 | 100 μg (2 ml/L) |

Purification Protocol for GGF2
  All procedures are done at 4° C.
  Chemicals:
  Sodium Acetate
  Glacial Acetic Acid (for pH adjustment)
  10N NaOH (for pH adjustment)
  NaCl
  Sodium Sulfate
  L-Arginine (JT Baker cat #: 2066-06)
  Mannitol (IT Baker cat #: 2553-01)
  Starting material: Conditioned media supernatant. Adjust pH to 6.5.
Step 1:
  Capture-Cation Exchange Chropmatography
  HiPrep SP 16/10 (Amersham Biosciences)
  Column equilibration: Buffer A—5CV, buffer B—5CV, buffer 15% B—5CV
  Buffer A: 20 mM Na Acetate, pH 6.0
  Buffer B: 20 mM Na Acetate, pH 6.0, 1 M NaCl
  Load sample at 2 ml/min with a continuous load overnight if possible. Binding is better with continuous loading.
    Maximum capacity for a starting sample: 5 mg GGF2/ml media
    Flow rate: 3 ml/min
    First wash: 15% B, 10CV
    Second wash: 35% B, 10CV
    GGF2 elution: 60% B, 8CV
    Column wash: 100% B, 8CV

| Buffers: | Composition | Conductivity | Use |
|---|---|---|---|
| 15% B | 20 mM NaAcetate, pH 6.0, 150 mM NaCl | | Preequilibration First wash |
| 35% B | 20 mM NaAcetate, pH 6.0, 350 mM NaCl | | Second wash |
| 60% B | 20 mM NaAcetate, pH 6.0, 600 mM NaCl | | GGF2 elution |
| 100% B | 20 mM NaAcetate, pH 6.0, 1000 mM NaCl | 88 mS/cm | Column wash |

Step 2:
  Refinement—Gel Filtration Chromatography
  Sephacryl S200 26/60
  Elution buffer: 20 mM Na Acetate, 100 mM Sodium Sulfate, 1% mannitol, 10 mM L-Arginine, pH 6.5
  Buffer conductivity:
  Sample: SP GGF2 elution pool concentrated up to ~AU280 1.0
  Flow rate: 1.3 ml/min
  Peak elution: at ~0.36CV from injection start Step 3: DNA and Endotoxin Removal—Filtration Through Intercept Q Membrane.
  Preequilibration buffer: 20 mM Na Acetate, 100 mM Sodium Sulfate, 1% Mannitol, 10 mM L-Arginine, pH 6.5
  Collect flow through
Step 4; Final Formulation and Sample Preparation
  Add additional 90 mM L-Arginine to the sample
  Concentrate
  Sterile Filter The vehicle/control article used herein is 0.2% Bovine Serum Albumin (BSA), 0.1 M Sodium Phosphate, pH 7.6.

Rat strains CD®IGS [Crl:CD®(SD)/MYOINFARCT] and Naive Sprague Dawley are used herein. These strains were acquired from Charles River Laboratories. The test animals are approximately 6-7 weeks of age at arrival and weigh approximately 160-200 g, at the time of surgical procedure. The actual range may vary and is documented in the data.

All naive Sprague Dawley animals received were placed on study and assigned to Group 1. Animals considered suitable for study were weighed prior to treatment.

All CD®IGS [Crl:CD® (SD)/MYOINFARCT] animals received were randomized into treatment groups (Groups 2-5) using a simple randomization procedure based on calculated Ejection Fraction from Echocardiographic examinations performed on Day 7 post surgical procedure conducted at Charles River Laboratories. Simple randomization was conducted to result in each treatment group (Groups 2-5) consisting of applicable numbers of animals resulting in an approximately equal Group Mean Ejection Fraction (±3%) across Group 2-5.

All animals in Group 2-6 were acclimated at Charles River Laboratories according to Standard Operating Procedures of that laboratory. Animals were subsequently randomized into treatment groups. All naive animals in Group 1 were acclimated for approximately 24 hours post receipt prior to their primary Echocardiographic examinations.

The animals were individually housed in suspended, stainless steel, wire-mesh type cages, Solid-bottom cages were not used in general because rodents are coprophagic and the ingestion of feces containing excreted test article and metabolic products or ingestion of the bedding itself could confound the interpretation of the results in this toxicity study.

Fluorescent lighting was provided via an automatic timer for approximately 12 hours per day. On occasion, the dark cycle was interrupted intermittently due to study-related activities. Temperature and humidity were monitored and recorded daily and maintained to the maximum extent possible between 64 to 79° F. and 30 to 70%, respectively.

The basal diet was block Lab Diet® Certified Rodent Diet #5002, PMI Nutrition International, Inc. This diet was available ad libitum unless designated otherwise. Each lot number used was identified in the study records. Tap water was supplied ad libitum to all animals via an automatic water system unless otherwise indicated.

Study Designs

TABLE 5

GGF2 versus EGF-Id fragment (Liu et al., 2006)
Dosed for 10 days starting day 7 after LAD

| Group | Treatment | In-Life Duration | Dose | Dosing Interval† | ECHO Time Points (post-op) |
|---|---|---|---|---|---|
| 1 (n = 5M; n = 5 F) | Control (Vehicle) | 17 days post-op | Vehicle only | 24 Hr | Day 6, 17 |
| 2 (n= 6M; n = 6 F) | GGF2 | 17 days post | 0.0625 mg/kg | 24 Hr | Day 6, 17 |
| 3 (n= 6M; n = 6 F) | GGF2 | 17 days post | 0.625 mg/kg | 24 Hr | Day 6, 17 |
| 4 (n = 6M; n = 7 F) | EGF-Id | 17 days post | Equimolar | 24 Hr | Day 6, 17 |
| 5 (n = 7M; n = 6 F) | EGF-Id | 17 days post | Equimolar | 24 Hr | Day 6, 17 |

TABLE 6

GGF2 higher dose compared with EGF-Id and EGF-Ig Dosed
for 20 days starting day 7 after LAD. 10 day washout.

| Group | Treatment | In-Life Duration | Dose | Dosing Interval† | ECHO Time Points (post-op) |
|---|---|---|---|---|---|
| 1 (n = 5M; n = 5 F) | N/A: Age Matched Naïve controls | 30 days post primary ECHO | NA | NA | ‡Day 1, 12, 22, & 32 |
| 2 (n = 6M; n = 6 F) | Control (Vehicle) | 38 days post-op | Vehicle only | 24 Hr | *Day 7, 18, 28, & 38 |
| 3 (n = 6M; n = 6 F) | GGF-2 | 38 days post-op | 0.625 mg/kg | 24 Hr | *Day 7, 18, 28, & 38 |
| 4 (n = 6M; n = 7 F) | GGF-2 | 38 days post-op | 3.25 mg/kg | 24 Hr | *Day 7, 18, 28, & 38 |
| 5 (n = 7M; n = 6 F) | EGF-Id | 38 days post-op | Equimolar | 24 Hr | *Day 7, 18, 28, & 38 |
| 6 (n = 7M; n = 6 F) | EGF-Ig | 38 days post-op | Equimolar | 24 Hr | *Day 7, 18, 28, & 38 |

TABLE 7

GGF2 Dose frequency

| Group | Treatment | In-Life Duration | Dose | Dosing Interval† | ECHO Time Points (post-op) |
|---|---|---|---|---|---|
| 1 (n = 5M; n = 5 F) | N/A: Age Matched Naïve controls | 30 days post primary ECHO | NA | NA | ‡Day 1, 12, 22, & 32 |
| 2 (n = 6M; n = 6 F) | Control (Vehicle) | 38 days post-op | Vehicle only | 24 Hr | *Day 7, 18, 28, & 38 |
| 3 (n = 6M; n = 6 F) | GGF-2 | 38 days post-op | 3.25 mg/kg | 24 Hr | *Day 7, 18, 28, & 38 |
| 4 (n = 6M; n = 7 F) | GGF-2 | 38 days post-op | 3.25 mg/kg | 48 Hr | *Day 7, 18, 28, & 38 |
| 5 (n = 7M; n = 6 F) | GGF-2 | 38 days post-op | 3.25 mg/kg | 96 Hr | *Day 7, 18, 28, & 38 |

TA 1—Test Article 1;

M = males;

F = females.

TABLE 8

GGF2 with and without BSA

| Group | Treatment | In-Life Duration | Dose | Dosing Interval† | ECHO Time Points (post-op) |
|---|---|---|---|---|---|
| 1 (n = 5M; n = 5 F) | N/A: Age Matched Naive controls | 17 days post-op | NA | NA | Day 6 and 17 |
| 2 (n = 6M; n = 6 F) | Control (Vehicle) | 17 days post | Vehicle only | 24 Hr | Day 6 and 17 |
| 3 (n = 6M; n = 6 F) | GGF-2 + BSA | 17 days post | 3.25 mg/kg | 24 Hr | Day 6 and 17 |
| 4 (n = 6M; n = 7 F) | GGF-2 without BSA | 17 days post | 3.25 mg/kg | 24 Hr | Day 6 and 17 |

Test and Control Article Administration
Route of Administration

The test and control articles were administered by intravenous injection. Animals assigned to Group 1 were not treated with vehicle or Test Articles; these animals served as age matched controls without treatment. Frequency of administration, duration, and dose were as described in the Tables 5-8. The dose volume was approximately 1 ml per kg.

Test Article Administration

The test and control articles were administered via the tail vein. Individual doses were based on the most recent body weights. The dose was administered by bolus injection, unless otherwise indicated by the Sponsor.

Preparation of Test System

Surgical Procedure—Left Anterior Descending Artery Ligation

The surgical procedures were performed at Charles River Laboratories as described in Charles River Laboratories *Surgical Capabilities Reference Paper*, Vol. 13, No. 1, 2005. Briefly, a cranio-caudal incision is made in the chest, slightly to the left of the sternum, through skin and the pectoral muscles. The third and forth ribs are transected, and the intercostals muscles are blunt dissected. The thoracic cavity is rapidly entered, and the pericardium completely opened. The heart is exteriorized through the incision. The pulmonary cone and left auricle are identified. A small curved needle is used to pass a piece of 5-0 silk suture under the left anterior descending coronary artery. The ligature is tied, and the heart is replaced into the thorax. The air in the thoracic cavity is gently squeezed out while the thoracic wall and skin incision is closed. The animal is resuscitated using positive pressure ventilation and placed in an oxygen rich environment.

Post-Operative Recovery

Short term post-operative monitoring and administration of appropriate analgesics were performed by Charles River Laboratories as described in Charles River Laboratories *Surgical Capabilities Reference Paper*, Vol. 13, No. 1, 2005.

Long term post-operative monitoring was conducted to assess the animals for signs of pain or infection. Daily incision site observations continued for 7 days post receipt of animals. Supplemental pain management and antimicrobial therapy were administered as necessitated.

TABLE 9

SCHEDULED MEDICATIONS AND DOSAGES

| | INTERVAL, DOSE, AND ROUTE | | | | |
|---|---|---|---|---|---|
| DRUG | DAILY POSTSURGERY | DAY 1/7* ECHO | DAY 12/18* ECHO | DAY 22/28* ECHO | DAY 32/38* ECHO & Necropsy |
| Isoflurane | — | To effect, inhalation | To effect, inhalation | To effect, inhalation | To effect, inhalation |
| Buprenorphine | 0.01 mg/kg, I.M. (only as needed) | — | — | — | — |

*ECHO procedure Day defined by animal Group assignment as indicated below.

Antemortem Study Evaluations
Cageside Observations

All animals were observed at least twice a day for morbidity, mortality, injury, and availability of food and water. Any animals in poor health were identified for further monitoring and possible euthanasia.

Body Weights

Body weights were measured and recorded at least once prior to randomization and weekly during the study.

Food Consumption

Food consumption was not measured, but inappetence was documented.

Echocardiographic Examinations

Echocardiographic examinations were conducted on all animals assigned to Group 1 on Day 1, 12, 22 and Day 32 post receipt (Day 0). Echocardiographic examinations were conducted on all animals assigned to Group 2-5 on Day 7, 18, 28 and Day 38 post-surgical procedure conducted at Charles River Laboratories (Day 0).

For the echocardiographic examination, each animal was anesthetized according to Table 5 and its hair clipped from the thorax. Coupling gel was applied to the echocardiographic transducer and image obtained to measure cardiac function at multiple levels. Images were obtained for each animal in short axis view (at mid-papillary level, or other depending on location of observed infarct area by echocardiography).

Echocardiographic Parameters

ECHO images were taken at the mid-papillary muscle level, or other depending on location of observed infarct area by echocardiography, of the left ventricle. M-mode and 2-D images were recorded and stored on CD and/or MOD. Measurement parameters obtained with ECHO include: Intraventricular Septal Wall Thickness (diastole); units=cm; Intraventricular Septal Wall Thickness (systole); units=cm; Left Ventricular Internal Dimension (diastole); units=cm; Left Ventricular Internal Dimension (systole); units=cm; Left Ventricular Papillary Wall Thickness (diastole); units=cm; Left Ventricular Papillary Wall Thickness (systole); units=cm; End Diastolic Volume; units=mL; End Systolic Volume; units=mL; Ejection Fraction; reported as a percentage; Stroke Volume; units=ml; and Percent Fractional Shortening; reported as a percentage Euthanasia Moribundity Any moribund animals, as defined by a Testing Facility Standard Operating Procedure, were euthanized for humane reasons. All animals euthanized in extremis or found dead were subjected to a routine necropsy.

Method of Euthanasia

Euthanasia was performed by saturated potassium chloride injection into the vena cava followed by an approved method to ensure death, e.g. exsanguination.

Final Disposition

All surviving animals placed on study were euthanized at their scheduled necropsy or, if necessary, euthanized in extremis.

Results

Study 1—Treatment of rats with GGF2 at 0.625 mg/kg iv qday resulted in significant improvement of cardiac function as shown here by changes in Ejection Fraction and Fractional Shortening. EGF-1d fragment did not result in the same degree of improvement. See Table 5.

Study 2—Treatment of rats with GGF2 at 0.625 and 3.25 mg/kg iv qday resulted in significant improvement of cardiac function as shown here by changes in Ejection Fraction and Fractional Shortening. Significant improvements were also seen in end systolic and diastolic volumes during the treatment period. See Table 6.

Study 3 Results—Treatment of rats with GGF2 3.25 mg/kg iv q24, 48 or 96 hours resulted in significant improvement of cardiac function as shown here by changes in Ejection Fraction and Fractional Shortening. Significant improvements were also seen in end systolic and diastolic volumes during the treatment period. See Table 7.

Previous reports (Liu et al) have shown that a carrier protein such as BSA is required for optimal neuregulin stability and activity. GGF2 has demonstrated stability without carriers such as BSA. This experiment was designed to test whether GGF2 is stable and active in a therapeutic regimen without BSA. After 10 days of treatment, both the BSA and non-BSA containing GGF2 formulations resulted in improvements in ejection fraction compared with vehicle controls similar to those seen in previous studies. It is, therefore, evident from this study that BSA or other carrier protein is not required in GGF2 formulations for the treatment of CHF. See Table 8.

TABLE 10

Pathology findings

| Dosing | Sciatic Nerve Sheath Hyperplasia (NSH) | Mammary NSH | Injection site/Skin changes | Cardiac effects |
|---|---|---|---|---|
| Daily s.c. | ++ | ++ | ++ | + |
| Daily i.v. | + | + | + | +/− |
| 48 hour interval i.v. | +/− | − | − | +/−− |
| 96 hour interval i.v. | − | − | − | − |

++ frequently present;
+ present;
+/− occasionally observed,
− rare or not observed As shown in Table 10, intermittent dosing of GGF2 reduces side effects associated with supranormal levels of exogenously administered GGF2. The present inventors have discovered that this finding holds true irrespective of whether the GGF2 is administered intravenously or subcutaneously.

The hyperplasia and cardiac effects are sometimes seen with every other day dosing. We have not seen with less frequent dosing.

Several publications and patent documents are referenced in this application in order to more fully describe the state of the art to which this invention pertains. All publications and patent applications mentioned in this specification are herein incorporated by reference to the same extent as if each independent publication or patent application was specifically and individually indicated to be incorporated by reference.

What is claimed is:

1. A method of reducing side effects due to supraphysiological levels of a peptide comprising an epidermal growth factor-like (EGF-like) domain of glial growth factor 2 (GGF2) upon administration while treating or preventing heart failure in a mammal over a prolonged duration, said method comprising:

administering a therapeutically effective amount of said peptide to said mammal at an interval of at least 96 hours, wherein said therapeutically effective amount is effective to reduce side effects due to supraphysiological levels of said peptide while treating or preventing heart failure in said mammal.

2. The method according to claim 1, wherein said side effects are nerve sheath hyperplasia, mammary hyperplasia, renal nephropathy, hypospermia, hepatic enzyme elevation, heart valve changes, or skin changes.

3. The method according to claim 1, wherein said peptide administered at an interval of at least 96 hours elicits fluctuations in the serum levels of said peptide.

4. The method according to claim 1, wherein said peptide administered at an interval of at least 96 hours does not maintain steady state therapeutic levels of said peptide in the serum of said subject.

5. The method according to claim 1, wherein said subject is exposed to a cardiotoxic agent.

6. The method according to claim 5, wherein said cardiotoxic agent is cocaine, alcohol, an anti-ErbB2 antibody, an anti-HER2 antibody, and/or an anthracycline antibiotic.

7. The method according to claim 6, wherein said subject is exposed to said anti-ErbB2 or said anti-HER2 antibody during or after anthracycline antibiotic exposure.

8. The method according to claim 5, wherein said peptide is administered prior to exposure to said cardiotoxic agent.

9. The method according to claim 5, wherein said peptide is administered after exposure to said cardiotoxic agent.

10. The method according to claim 1, wherein said subject is suffering from myocarditis, thyroid disease, viral infection, gingivitis, drug abuse, alcohol abuse, periocarditis, atherosclerosis, vascular disease, hypertrophic cardiomyopathy, acute myocardial infarction, previous myocardial infarction, left ventricular systolic dysfunction, coronary bypass surgery, starvation, radiation exposure, an eating disorder, and/or a genetic defect.

11. The method according to claim 1, wherein said peptide is a recombinant human GGF2 or a fragment thereof.

12. The method according to claim 1, wherein said peptide comprises a polypeptide sequence:

(SEQ ID NO: 4)
SHLVKCAEKEKTFCVNGGECFMVKDLSNPSRYLCKCPNEFTGDRCQNYV

MASFYSTSTPFLSLPE.

* * * * *